(12) United States Patent
Atkinson et al.

(10) Patent No.: US 9,790,477 B2
(45) Date of Patent: Oct. 17, 2017

(54) TRANSPOSON VECTOR FOR VERTEBRATE AND INVERTEBRATE GENETIC MANIPULATION

(71) Applicant: The Regents of the University of California, Oakland, CA (US)

(72) Inventors: Peter W. Atkinson, Riverside, CA (US); Susan R. Wessler, Claremont, CA (US); Kun Liu, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/946,657

(22) Filed: Nov. 19, 2015

(65) Prior Publication Data

US 2016/0177334 A1    Jun. 23, 2016

Related U.S. Application Data

(60) Provisional application No. 62/081,947, filed on Nov. 19, 2014.

(51) Int. Cl.
| | | |
|---|---|---|
| *C07H 21/04* | (2006.01) | |
| *C12N 15/74* | (2006.01) | |
| *C12N 15/63* | (2006.01) | |
| *C12N 9/12* | (2006.01) | |
| *C12N 15/81* | (2006.01) | |
| *C12N 15/90* | (2006.01) | |
| *A01K 67/00* | (2006.01) | |

(52) U.S. Cl.
CPC ........... *C12N 9/1241* (2013.01); *C12N 15/63* (2013.01); *C12N 15/81* (2013.01); *C12N 15/90* (2013.01); *C12N 2800/90* (2013.01); *C12Y 207/07* (2013.01)

(58) Field of Classification Search
CPC .. C12N 9/1241; C12N 2800/90; C12N 15/90; C12N 15/63; C12N 15/81; C12Y 207/07
See application file for complete search history.

(56) References Cited

PUBLICATIONS

Guo et al. Protein tolerance to random amino acid change. PNAS 101:9205-9210, 2004.*
Lobo et al. Analysis of 14 BAC sequences from the Aedes aegypti genome. Genome Biology 8:R88.1-R88.12, 2007.*
Atkinson, Peter W., "The Muta1 Transposon from the Mosquito *Aedes aegypti* is Active in its Host Insect and a Range of Organisms," Presentation, Mobile Genetic Elements and Genome Evolution Conference, hosted by Keystone Symposia in Santa Fe, NM USA, Mar. 13, 2014, pp. 1-16.
Han et al., "MITE-Hunter: a program for discovering miniature inverted-repeat transposable elements from genomic sequences," Nucleic Acids Research, 2010, 38(22): 1-8.
Shah et al, "The Muta1 Transposon from the Mosquito *Aedes aegypti* is Active in its Host Insect and a Range of Organisms," Abstract, Mobile Genetic Elements and Genome Evolution Conference, hosted by Keystone Symposia in Santa Fe, NM USA, Mar. 10, 2014, pp. 1; available Mar. 2, 2014.
Shah et al, "The Muta1 Transposon from the Mosquito *Aedes aegypti* is Active in its Host Insect and a Range of Organisms," Poster, Mobile Genetic Elements and Genome Evolution Conference, hosted by Keystone Symposia in Santa Fe, NM USA, Mar. 10, 2014, pp. 1.
Yuan et al., "The catalytic domain of all eukaryotic cut-and-paste transposase superfamilies," PNAS, May 10, 2011, 108(19):7884-7889.

* cited by examiner

*Primary Examiner* — Quang Nguyen
(74) *Attorney, Agent, or Firm* — Kilpatrick Townsend & Stockton LLP

(57) ABSTRACT

The present invention provides a transposon for use in genetic manipulation of vertebrate and invertebrate cells.

12 Claims, 3 Drawing Sheets

Figure 2

```
................CGAGTTGGTTGGACT          GGTTGGACTTGAATTG................
``` in HEK293 cells

No.
| | | |
|---|---|---|
| 7 | ................CGAGTTGGTTGG | TTGGACTTGAATTG.................. |
| 4 | ................CGAGTTGGTTGGACT | TGAATTG.............. |
| 2 | 26 bp deletion | GGTTGGACTTGAATTG................. |
| 1 | ................CGAGTTGGTTGG | TCGACTTGAATTG.................. |
| 1 | ................CGAGTTGGTTGGACT | TGGACTTGAATTG................. |
| 1 | ................CGAGTTGGTTGG | GTTGGACTTGAATTG................ |
| 1 | ................CGA | GGTTGGACTTGAATTG................ |
| 1 | ................CGAGTTGGTTGGACT | TTGGACTTGAATTG................ |
| 1 | ................CGAGTT | AATTG.................. |
| 1 | ................CGAGTTGGTTGGAC | GACTTGAATTG.................. |
| 1 | 8 bp deletion | TGTTGGACTTGAATTG.................. |
| 1 | ................CGAGTTGGTTGGACT | GGACTTGAATTG.................. |
| 1 | ................CGAGTTGGTTGGACT | GGGTCTACTTGAATTG.................. |
| 1 | ................CGAGTTGGTTGG | GACTTGAATTG................ |
| 1 | ................CGAGTTGGT | GGTTGGACTTGAATTG.................. |
| 1 | 9bp deletion..insertion of 36bp DNA of unknown origin.. | TTGGACTTGAATTG................... | in HeLa cells

No.
| | | |
|---|---|---|
| 6 | ................CGAGTTGGTTGG | TTGGACTTGAATTG.............. |
| 6 | ................CGAGTTGGTTGGACT | TGAATTG................ |
| 3 | ................CGAGTTGGTTGGAC | GGACTTGAATTG.............. |
| 1 | ................CGAGTTGGTT | ACTTGAATTG.............. |
| 1 | ................CGAGTTGGTTGGAC | GGTTGGACTTGAATTG.............. |
| 1 | ................CGAGTTGGTTGGA | GGTTGGACTTGAATTG.............. |
| 1 | ................CGAGTTGGTTG | TTGGACTTGAATTG.............. |
| 1 | ................CGAGTTGGTTGG | GACTTGAATTG.............. |
| 1 | ................CGAGTTGGTTGG | TTAGACTTGAATTG.............. |
| 1 | ................CGAGTTGGTTG | ACTTGAATTG.............. |
| 1 | ................CGAGTTGGTTGGACT.. insertion of 148 bp human DNA.. | GACTTGAATTG.............. * |
| 1 | ................CGAGTTGGTTGGACT.. Muta L TIR seq GGGTCTAC..insertion of 32bp of E.coli DNA | TTGGACTTGAATTG..............** |
| 1 | ................CGAGTTGGTTGGACT | deletion of 31bp............ |
| 1 | ................CGAGTTGGTTGGAC | CTTGAATTG.............. |
| 1 | ................CGAGTTGGTTGGACT..insertion of 41bp unknown DNA.. | TGAATTG.............. |

*Human insertion is from chromosome 2, EF-hand domain protein.
** E. coli DNA is AMP nucleosidase gene. May be other gram(-) bacterial origin as well. Source unclear.

SEQUENCE LISTING

```
<160> NUMBER OF SEQ ID NOS: 62

<210> SEQ ID NO 1
<211> LENGTH: 3198
<212> TYPE: DNA
<213> ORGANISM: Artificial Sequence
<220> FEATURE:
<223> OTHER INFORMATION: synthetic nucleic acid sequence Muta1 from A.
      aegypti Liverpool strain

<400> SEQUENCE: 1
gggtctaccc cgtttggcat aatgccgttt ggcataatgc cgtttggcat acagtcgttt        60
ggcataaagt cgtttggcat aatagtcatt tggcataaca gtcgtttggc ataatggtca       120
tttggcataa tggtcgtttg gcataatttg aaaagaagct ttagattaaa taataaaaaa       180
caaaacatat acatgatgaa catctttatc tagtcgtacg cttctcacac tgttatgggt       240
cactttgtca cgatccatta gtcactgttt ttcaaatgta tttcaaatga aaatgcctta       300
tactagttta tttgatattt gtactacgaa gctggaaatg ttttaacgaa taacttgtca       360
tgataaataa taattacaca agtctcagtt taatcatggg atgaattggt tgagtatgcg       420
gataacgtga tctaaaaaat aagaagtttg tttatttta tttatgtttt attagccaat       480
gatttctcta ttttttgca gtaccattca agtattcaat tcgcttatga ctcatacaat       540
atgcataata ccgattctgt gttgttgcta gacaataata cttgaaaagt gagaatattt       600
cgtttcggta tcttttcaaaa ctatttcctt taacatcaac aataaagttc atccactctg       660
aagcgtcttg taatccattc acgtacaaaa atgttgtcaa tttaagtcgc tcttgatatt       720
tcaatgtctt ggatgcgatt atttttttga tattagaagg ccataaataa actggtccac       780
```

```
agacgtcttg gaacgtaaat agtggattcg ttatatcttc atattcacgg taaactttac    840
acattttgtt taaggattg ttcattttgt taactttaaa aacacttcaa tttatttaat      900
atacaaataa gccaaattaa ttaaaacttt tagcgataaa atcactcggc agacatgcgt    960
acgtaaaact gttacaattt tattcgaaca tgcctcgtcc aacacctgta atgcccgtaa   1020
atgcatgtca gtcccatgtt tgctggattt cctattcaca tgggacaatt atgcatttat   1080
gctcagtgta cctacctcat gcttaggaat tcaaatagaa cgcagcttgc tgtgatccaa   1140
ttgaatttaa aagtcaccca ttggtcgaaa aatcgaaaaa tttaaaatat gatcagtagg   1200
ctgtgaccac gttgtacccc gttgatactg gttgctaagt aacgaggccg gtatcattgt   1260
aagaggcata ctagtggaag ttggagaaag ggttctttc tgattctgct gtacggcggt    1320
ttagacgcga aaaatggact cggacagcga tagcgatttt tacggagtgg atgcagccga   1380
agcggaaaat gatgtgccga aagtgcttaa atcatccaga ggaaaggatt gtttggcttt   1440
caaaggattt ttattctatt caaacagaac accggtaagt ttttttttaa attgtgcgaa   1500
ataataatac aactaaaaac caaattaatg ttttagaatg gtcccaccca ctactgggaa   1560
tgtaggggta gaccacatgg acgcggctcg ggaagcagat gctctgcgcg tatggtaacg   1620
ttcaaggcgg ggaacgaaca ccgcgttctg tcatgttcgg accataacca cgaaagcgac   1680
ccaattcatt taatgggct aatgatgagg agttccctaa agcgacgggc caaccaaaac    1740
aatgcaacgc cagcgaaaat agtacgccaa gccggagcag aattttctaa tgcggtgcag   1800
cagaggatgt cgttaaatgc acaacgtaaa atcatcgacc gagtgcgaaa aagtgacgaa   1860
ctcccaaagg aacccacttc gttggccgaa tttgaggtgc cgatcagctt aaggacaacc   1920
gtcgatggag aatcttttcct tatgtctgat attaaggaag gaagcgacag agcaatcatt   1980
tttggtacgc tggaaggatt acgacgttta gcccttgcca aatactggat cgttgacgga   2040
acgttcgatt gcgttccagg tttgtttcgg caactgttca ccattcttgg tagcagttcg   2100
ccaaaccacg aacatgcgtt ccccataata cacacgttga tgacagcaaa aaatgaagcg   2160
ctgtatcggg cagtctttgc aacgctaata gaaaaggcaa atgagctggg gatcgatcta   2220
gatccaccag tcattttatc agattttgaa aaggctatca tcaacgctat aaaatctgag   2280
ttcccagaaa caaagcaaaa tgcgtgcttc tttcacctgt cccagaattt ctggaaaaga   2340
attcaagagg caaagcttat tggagaaatg accaacaata tcgccctgta tcatttcttc   2400
aaaaagacgc aagcccttgc ttttttacca actgaacgta taccagccgc gtttgagaat   2460
ttgaaaaaaa atgcgcctgt tcaactgaag gattttatat cttatgtgga cgaatactac   2520
attatgggtc gtgtccggcg tatcggaaag gatgggcgaa tcgttcgtac agaaccactg   2580
tacccgccgt cgttgtggtc gatttatgac aacgttttgt caaacgttcc gcgtaccaca   2640
aaccagattg aagcctggca ccgacgttgg caaacactgg tagcacgtca aactggagtg   2700
atcaagctga tgggtgagtt aaggctggag gaaaaatata cggttggaca aatcgcagct   2760
cttctggctg gtacgtccag caagcagaag aagacgatgc atcaaattaa tgatcaagcg   2820
gtgaagaata ttgttgaaaa tattgataaa tatcaggaaa ctgattatct tgaggcaatt   2880
gcagctcact taggatcaaa atcaaaataa gagagaggtt tttcattaca tttctatgta   2940
tacataacaa aaattgaaat aataaatgaa ttggtaaata tatatttctt ttcattgact   3000
catgtgaaca acgtaacaa aaatgttttta aaaatacgat ttctggttat ggttatgcca   3060
aacgactatt atgccaaatg accattatgc caaatgacta ttatgccaaa tggcattatg   3120
```

```
ccaaacgact attatgccaa acgactgtat gccaaacggc attatgccaa acggcattat    3180
gccaaacggg gtagaccc                                                  3198
```

<210> SEQ ID NO 2
<211> LENGTH: 504
<212> TYPE: PRT
<213> ORGANISM: Artificial Sequence
<220> FEATURE:
<223> OTHER INFORMATION: synthetic amino acid sequence Muta1 from A.
      aegypti Liverpool strain

<400> SEQUENCE: 2

```
Met Asp Ser Asp Ser Asp Ser Asp Phe Tyr Gly Val Asp Ala Ala Glu
1               5                   10                  15

Ala Glu Asn Asp Val Pro Lys Val Leu Lys Ser Ser Arg Gly Lys Asp
            20                  25                  30

Cys Leu Ala Phe Lys Gly Phe Leu Phe Tyr Ser Asn Arg Thr Pro Asn
        35                  40                  45

Gly Pro Thr His Tyr Trp Glu Cys Arg Gly Arg Pro His Gly Arg Gly
    50                  55                  60

Ser Gly Ser Arg Cys Ser Ala Arg Met Val Thr Phe Lys Ala Gly Asn
65                  70                  75                  80

Glu His Arg Val Leu Ser Cys Ser Asp His Asn His Glu Ser Asp Pro
                85                  90                  95

Ile His Leu Met Gly Leu Met Met Arg Ser Ser Leu Lys Arg Arg Ala
            100                 105                 110

Asn Gln Asn Asn Ala Thr Pro Ala Lys Ile Val Arg Gln Ala Gly Ala
        115                 120                 125

Glu Phe Ser Asn Ala Val Gln Gln Arg Met Ser Leu Asn Ala Gln Arg
    130                 135                 140

Lys Ile Ile Asp Arg Val Arg Lys Ser Asp Glu Leu Pro Lys Glu Pro
145                 150                 155                 160

Thr Ser Leu Ala Glu Phe Glu Val Pro Ile Ser Leu Arg Thr Thr Val
                165                 170                 175

Asp Gly Glu Ser Phe Leu Met Ser Asp Ile Lys Glu Gly Ser Asp Arg
            180                 185                 190

Ala Ile Ile Phe Gly Thr Leu Glu Gly Leu Arg Arg Leu Ala Leu Ala
        195                 200                 205

Lys Tyr Trp Ile Val Asp Gly Thr Phe Asp Cys Val Pro Gly Leu Phe
    210                 215                 220

Arg Gln Leu Phe Thr Ile Leu Gly Ser Ser Pro Asn His Glu His
225                 230                 235                 240

Ala Phe Pro Ile Ile His Thr Leu Met Thr Ala Lys Asn Glu Ala Leu
                245                 250                 255

Tyr Arg Ala Val Phe Ala Thr Leu Ile Glu Lys Ala Asn Glu Leu Gly
            260                 265                 270

Ile Asp Leu Asp Pro Pro Val Ile Leu Ser Asp Phe Glu Lys Ala Ile
        275                 280                 285

Ile Asn Ala Ile Lys Ser Glu Phe Pro Glu Thr Lys Gln Asn Ala Cys
    290                 295                 300

Phe Phe His Leu Ser Gln Asn Phe Trp Lys Arg Ile Gln Glu Ala Lys
305                 310                 315                 320

Leu Ile Gly Glu Met Thr Asn Asn Ile Ala Leu Tyr His Phe Lys
                325                 330                 335

Lys Thr Gln Ala Leu Ala Phe Leu Pro Thr Glu Arg Ile Pro Ala Ala
```

```
                    340                 345                 350
Phe Glu Asn Leu Lys Lys Asn Ala Pro Val Gln Leu Lys Asp Phe Ile
            355                 360                 365

Ser Tyr Val Asp Glu Tyr Tyr Ile Met Gly Arg Val Arg Arg Ile Gly
        370                 375                 380

Lys Asp Gly Arg Ile Val Arg Thr Glu Pro Leu Tyr Pro Pro Ser Leu
385                 390                 395                 400

Trp Ser Ile Tyr Asp Asn Val Leu Ser Asn Val Pro Arg Thr Thr Asn
                405                 410                 415

Gln Ile Glu Ala Trp His Arg Arg Trp Gln Thr Leu Val Ala Arg Gln
            420                 425                 430

Thr Gly Val Ile Lys Leu Met Gly Glu Leu Arg Leu Glu Glu Lys Tyr
        435                 440                 445

Thr Val Gly Gln Ile Ala Ala Leu Leu Ala Gly Thr Ser Ser Lys Gln
            450                 455                 460

Lys Lys Thr Met His Gln Ile Asn Asp Gln Ala Val Lys Asn Ile Val
465                 470                 475                 480

Glu Asn Ile Asp Lys Tyr Gln Glu Thr Asp Tyr Leu Glu Ala Ile Ala
                485                 490                 495

Ala His Leu Gly Ser Lys Ser Lys
            500

<210> SEQ ID NO 3
<211> LENGTH: 146
<212> TYPE: DNA
<213> ORGANISM: Artificial Sequence
<220> FEATURE:
<223> OTHER INFORMATION: synthetic nucleotide sequence - 146 bp ITR at
      the left end of the Muta1 transposon

<400> SEQUENCE: 3
gggtctaccc cgtttggcat aatgccgttt ggcataatgc cgtttggcat acagtcgttt      60
ggcataaagt cgtttggcat aatagtcatt tggcataaca gtcgtttggc ataatggtca     120
tttggcataa tggtcgtttg gcataa                                          146

<210> SEQ ID NO 4
<211> LENGTH: 146
<212> TYPE: DNA
<213> ORGANISM: Artificial Sequence
<220> FEATURE:
<223> OTHER INFORMATION: synthetic nucleotide sequence - 146 bp ITR at
      the right end of the Muta1 transposon

<400> SEQUENCE: 4
ttatgccaaa cgactattat gccaaatgac cattatgcca aatgactatt atgccaaatg      60
gcattatgcc aaacgactat tatgccaaac gactgtatgc caaacggcat tatgccaaac     120
ggcattatgc caaacggggt agaccc                                          146

<210> SEQ ID NO 5
<211> LENGTH: 20
<212> TYPE: DNA
<213> ORGANISM: Artificial Sequence
<220> FEATURE:
<223> OTHER INFORMATION: synthetic nucleotide primer

<400> SEQUENCE: 5
tctggagggt tgattgtttg                                                  20
```

```
<210> SEQ ID NO 6
<211> LENGTH: 20
<212> TYPE: DNA
<213> ORGANISM: Artificial Sequence
<220> FEATURE:
<223> OTHER INFORMATION: synthetic nucleotide primer

<400> SEQUENCE: 6
ctgaaggtgg tccgtcttac                                                   20

<210> SEQ ID NO 7
<211> LENGTH: 22
<212> TYPE: DNA
<213> ORGANISM: Artificial Sequence
<220> FEATURE:
<223> OTHER INFORMATION: synthetic nucleotide primer

<400> SEQUENCE: 7
caccatggac tcggacagcg at                                                22

<210> SEQ ID NO 8
<211> LENGTH: 40
<212> TYPE: DNA
<213> ORGANISM: Artificial Sequence
<220> FEATURE:
<223> OTHER INFORMATION: synthetic nucleotide primer

<400> SEQUENCE: 8
cagtagtggg tgggaccatt cggtgttctg tttgaataga                             40

<210> SEQ ID NO 9
<211> LENGTH: 25
<212> TYPE: DNA
<213> ORGANISM: Artificial Sequence
<220> FEATURE:
<223> OTHER INFORMATION: synthetic nucleotide primer

<400> SEQUENCE: 9
ttattttgat tttgatccta agtga                                             25

<210> SEQ ID NO 10
<211> LENGTH: 40
<212> TYPE: DNA
<213> ORGANISM: Artificial Sequence
<220> FEATURE:
<223> OTHER INFORMATION: synthetic nucleotide primer

<400> SEQUENCE: 10
cagtagtggg tgggaccatt cggtgttctg tttgaataga                             40

<210> SEQ ID NO 11
<211> LENGTH: 19
<212> TYPE: DNA
<213> ORGANISM: Artificial Sequence
<220> FEATURE:
<223> OTHER INFORMATION: synthetic nucleotide primer

<400> SEQUENCE: 11
tggagaaggg tatggagga                                                    19

<210> SEQ ID NO 12
<211> LENGTH: 19
<212> TYPE: DNA
<213> ORGANISM: Artificial Sequence
<220> FEATURE:
<223> OTHER INFORMATION: synthetic nucleotide primer
```

<400> SEQUENCE: 12
ggcaggacgg acatttatt                                                    19

<210> SEQ ID NO 13
<211> LENGTH: 56
<212> TYPE: DNA
<213> ORGANISM: Artificial Sequence
<220> FEATURE:
<223> OTHER INFORMATION: synthetic nucleotide primer

<400> SEQUENCE: 13
taacaatcaa gaaaacaag aaaatcggac ttcaaatggg gtctaccccg tttggc           56

<210> SEQ ID NO 14
<211> LENGTH: 53
<212> TYPE: DNA
<213> ORGANISM: Artificial Sequence
<220> FEATURE:
<223> OTHER INFORMATION: synthetic nucleotide primer

<400> SEQUENCE: 14
caactgttct agaatccata cttgatccat ttgaagggtc taccccgttt ggc             53

<210> SEQ ID NO 15
<211> LENGTH: 57
<212> TYPE: DNA
<213> ORGANISM: Artificial Sequence
<220> FEATURE:
<223> OTHER INFORMATION: synthetic nucleotide primer

<400> SEQUENCE: 15
taacaatcaa gaaaacaag aaaatcggac cttcaaatgg ggtctacccc gtttggc          57

<210> SEQ ID NO 16
<211> LENGTH: 54
<212> TYPE: DNA
<213> ORGANISM: Artificial Sequence
<220> FEATURE:
<223> OTHER INFORMATION: synthetic nucleotide primer

<400> SEQUENCE: 16
caactgttct agaatccata cttgatccat ttgaaggggt ctaccccgtt tggc            54

<210> SEQ ID NO 17
<211> LENGTH: 48
<212> TYPE: DNA
<213> ORGANISM: Artificial Sequence
<220> FEATURE:
<223> OTHER INFORMATION: synthetic nucleotide primer

<400> SEQUENCE: 17
taacaatcaa gaaaacaag aaaatcggac gggtctaccc cgtttggc                    48

<210> SEQ ID NO 18
<211> LENGTH: 45
<212> TYPE: DNA
<213> ORGANISM: Artificial Sequence
<220> FEATURE:
<223> OTHER INFORMATION: synthetic nucleotide primer

<400> SEQUENCE: 18
caactgttct agaatccata cttgatcggg tctaccccgt ttggc                      45

<210> SEQ ID NO 19
<211> LENGTH: 40

```
<212> TYPE: DNA
<213> ORGANISM: Artificial Sequence
<220> FEATURE:
<223> OTHER INFORMATION: synthetic nucleotide primer

<400> SEQUENCE: 19
cgaagctgga aatgttttaa ctcttggcct cctctagtac                              40

<210> SEQ ID NO 20
<211> LENGTH: 40
<212> TYPE: DNA
<213> ORGANISM: Artificial Sequence
<220> FEATURE:
<223> OTHER INFORMATION: synthetic nucleotide primer

<400> SEQUENCE: 20
gtactagagg aggccaagag ttaaaacatt tccagcttcg                              40

<210> SEQ ID NO 21
<211> LENGTH: 40
<212> TYPE: DNA
<213> ORGANISM: Artificial Sequence
<220> FEATURE:
<223> OTHER INFORMATION: synthetic nucleotide primer

<400> SEQUENCE: 21
atacgaacag tatgatactc aggaaactga ttatcttgag                              40

<210> SEQ ID NO 22
<211> LENGTH: 40
<212> TYPE: DNA
<213> ORGANISM: Artificial Sequence
<220> FEATURE:
<223> OTHER INFORMATION: synthetic nucleotide primer

<400> SEQUENCE: 22
ctcaagataa tcagtttcct gagtatcata ctgttcgtat                              40

<210> SEQ ID NO 23
<211> LENGTH: 16
<212> TYPE: DNA
<213> ORGANISM: Artificial Sequence
<220> FEATURE:
<223> OTHER INFORMATION: synthetic nucleotide adapter

<400> SEQUENCE: 23
gacgatgagt cctgag                                                       16

<210> SEQ ID NO 24
<211> LENGTH: 14
<212> TYPE: DNA
<213> ORGANISM: Artificial Sequence
<220> FEATURE:
<223> OTHER INFORMATION: synthetic nucleotide adapter

<400> SEQUENCE: 24
tactcaggac tcat                                                         14

<210> SEQ ID NO 25
<211> LENGTH: 19
<212> TYPE: DNA
<213> ORGANISM: Artificial Sequence
<220> FEATURE:
<223> OTHER INFORMATION: synthetic nucleotide primer

<400> SEQUENCE: 25
```
gacgatgagt cctgagtag                                                19

<210> SEQ ID NO 26
<211> LENGTH: 19
<212> TYPE: DNA
<213> ORGANISM: Artificial Sequence
<220> FEATURE:
<223> OTHER INFORMATION: synthetic nucleotide primer

<400> SEQUENCE: 26
ttatgccaaa cgactgtat                                                19

<210> SEQ ID NO 27
<211> LENGTH: 17
<212> TYPE: DNA
<213> ORGANISM: Artificial Sequence
<220> FEATURE:
<223> OTHER INFORMATION: synthetic nucleotide primer

<400> SEQUENCE: 27
ccaaacgggg tagaccc                                                  17

<210> SEQ ID NO 28
<211> LENGTH: 32
<212> TYPE: DNA
<213> ORGANISM: Artificial Sequence
<220> FEATURE:
<223> OTHER INFORMATION: synthetic nucleotide primer

<400> SEQUENCE: 28
gataccggtc ttgttagcga gttggttgga ct                                 32

<210> SEQ ID NO 29
<211> LENGTH: 34
<212> TYPE: DNA
<213> ORGANISM: Artificial Sequence
<220> FEATURE:
<223> OTHER INFORMATION: synthetic nucleotide primer

<400> SEQUENCE: 29
aataccggtg gattaatccc aattcaagtc caac                               34

<210> SEQ ID NO 30
<211> LENGTH: 31
<212> TYPE: DNA
<213> ORGANISM: Artificial Sequence
<220> FEATURE:
<223> OTHER INFORMATION: synthetic nucleotide primer

<400> SEQUENCE: 30
cgcatgtgtt ttatcggtct gtatatcgag g                                  31

<210> SEQ ID NO 31
<211> LENGTH: 27
<212> TYPE: DNA
<213> ORGANISM: Artificial Sequence
<220> FEATURE:
<223> OTHER INFORMATION: synthetic nucleotide primer

<400> SEQUENCE: 31
cccatcacaa agctctgacc tcaatcc                                       27

<210> SEQ ID NO 32
<211> LENGTH: 27
<212> TYPE: DNA
<213> ORGANISM: Artificial Sequence

```
<220> FEATURE:
<223> OTHER INFORMATION: synthetic nucleotide primer

<400> SEQUENCE: 32
gctaactaga gaacccactg cttactg                                    27

<210> SEQ ID NO 33
<211> LENGTH: 21
<212> TYPE: DNA
<213> ORGANISM: Artificial Sequence
<220> FEATURE:
<223> OTHER INFORMATION: synthetic nucleotide primer

<400> SEQUENCE: 33
tgcagatgaa cttcagggtc a                                          21

<210> SEQ ID NO 34
<211> LENGTH: 10
<212> TYPE: DNA
<213> ORGANISM: Artificial Sequence
<220> FEATURE:
<223> OTHER INFORMATION: synthetic 8bp TSD flanking sequence for Muta1

<400> SEQUENCE: 34
gcttcaaatg                                                       10

<210> SEQ ID NO 35
<211> LENGTH: 33
<212> TYPE: DNA
<213> ORGANISM: Artificial Sequence
<220> FEATURE:
<223> OTHER INFORMATION: synthetic nucleotide primer

<400> SEQUENCE: 35
ctgacaaatg actcttgttg cagggctacg aac                             33

<210> SEQ ID NO 36
<211> LENGTH: 32
<212> TYPE: DNA
<213> ORGANISM: Artificial Sequence
<220> FEATURE:
<223> OTHER INFORMATION: synthetic nucleotide primer

<400> SEQUENCE: 36
tggaaaagga gccattaacg tggtcattgg ag                              32

<210> SEQ ID NO 37
<211> LENGTH: 10
<212> TYPE: DNA
<213> ORGANISM: Artificial Sequence
<220> FEATURE:
<223> OTHER INFORMATION: synthetic excision site sequence

<400> SEQUENCE: 37
aaaatcggac                                                       10

<210> SEQ ID NO 38
<211> LENGTH: 17
<212> TYPE: DNA
<213> ORGANISM: Artificial Sequence
<220> FEATURE:
<223> OTHER INFORMATION: synthetic excision site sequence

<400> SEQUENCE: 38
aaaatcggac gggtcta                                               17
```

```
<210> SEQ ID NO 39
<211> LENGTH: 23
<212> TYPE: DNA
<213> ORGANISM: Artificial Sequence
<220> FEATURE:
<223> OTHER INFORMATION: synthetic excision site sequence

<400> SEQUENCE: 39
aaaatcggac gggtctaccc cgt                                              23

<210> SEQ ID NO 40
<211> LENGTH: 16
<212> TYPE: DNA
<213> ORGANISM: Artificial Sequence
<220> FEATURE:
<223> OTHER INFORMATION: synthetic excision site sequence

<400> SEQUENCE: 40
ggtagtccca tcaagt                                                      16

<210> SEQ ID NO 41
<211> LENGTH: 12
<212> TYPE: DNA
<213> ORGANISM: Artificial Sequence
<220> FEATURE:
<223> OTHER INFORMATION: synthetic excision site sequence

<400> SEQUENCE: 41
ggacttcaat ag                                                          12

<210> SEQ ID NO 42
<211> LENGTH: 12
<212> TYPE: DNA
<213> ORGANISM: Artificial Sequence
<220> FEATURE:
<223> OTHER INFORMATION: synthetic excision site sequence

<400> SEQUENCE: 42
ttcaatagat ca                                                          12

<210> SEQ ID NO 43
<211> LENGTH: 13
<212> TYPE: DNA
<213> ORGANISM: Artificial Sequence
<220> FEATURE:
<223> OTHER INFORMATION: synthetic excision site sequence

<400> SEQUENCE: 43
ggacgcttga act                                                         13

<210> SEQ ID NO 44
<211> LENGTH: 13
<212> TYPE: DNA
<213> ORGANISM: Artificial Sequence
<220> FEATURE:
<223> OTHER INFORMATION: synthetic excision site sequence

<400> SEQUENCE: 44
gcttcaacta tca                                                         13

<210> SEQ ID NO 45
<211> LENGTH: 15
<212> TYPE: DNA
<213> ORGANISM: Artificial Sequence
<220> FEATURE:
<223> OTHER INFORMATION: synthetic excision site sequence
```

```
<400> SEQUENCE: 45
cgagttggtt ggact                                                    15

<210> SEQ ID NO 46
<211> LENGTH: 16
<212> TYPE: DNA
<213> ORGANISM: Artificial Sequence
<220> FEATURE:
<223> OTHER INFORMATION: synthetic excision site sequence

<400> SEQUENCE: 46
ggttggactt gaattg                                                   16

<210> SEQ ID NO 47
<211> LENGTH: 12
<212> TYPE: DNA
<213> ORGANISM: Artificial Sequence
<220> FEATURE:
<223> OTHER INFORMATION: synthetic excision site sequence

<400> SEQUENCE: 47
cgagttggtt gg                                                       12

<210> SEQ ID NO 48
<211> LENGTH: 14
<212> TYPE: DNA
<213> ORGANISM: Artificial Sequence
<220> FEATURE:
<223> OTHER INFORMATION: synthetic excision site sequence

<400> SEQUENCE: 48
ttggacttga attg                                                     14

<210> SEQ ID NO 49
<211> LENGTH: 16
<212> TYPE: DNA
<213> ORGANISM: Artificial Sequence
<220> FEATURE:
<223> OTHER INFORMATION: synthetic excision site sequence

<400> SEQUENCE: 49
ggttggactt gaattg                                                   16

<210> SEQ ID NO 50
<211> LENGTH: 14
<212> TYPE: DNA
<213> ORGANISM: Artificial Sequence
<220> FEATURE:
<223> OTHER INFORMATION: synthetic excision site sequence

<400> SEQUENCE: 50
tcggacttga attg                                                     14

<210> SEQ ID NO 51
<211> LENGTH: 13
<212> TYPE: DNA
<213> ORGANISM: Artificial Sequence
<220> FEATURE:
<223> OTHER INFORMATION: synthetic excision site sequence

<400> SEQUENCE: 51
tggacttgaa ttg                                                      13

<210> SEQ ID NO 52
```

```
<211> LENGTH: 15
<212> TYPE: DNA
<213> ORGANISM: Artificial Sequence
<220> FEATURE:
<223> OTHER INFORMATION: synthetic excision site sequence

<400> SEQUENCE: 52
gttggacttg aattg                                                    15

<210> SEQ ID NO 53
<211> LENGTH: 14
<212> TYPE: DNA
<213> ORGANISM: Artificial Sequence
<220> FEATURE:
<223> OTHER INFORMATION: synthetic excision site sequence

<400> SEQUENCE: 53
cgagttggtt ggac                                                     14

<210> SEQ ID NO 54
<211> LENGTH: 11
<212> TYPE: DNA
<213> ORGANISM: Artificial Sequence
<220> FEATURE:
<223> OTHER INFORMATION: synthetic excision site sequence

<400> SEQUENCE: 54
gacttgaatt g                                                        11

<210> SEQ ID NO 55
<211> LENGTH: 16
<212> TYPE: DNA
<213> ORGANISM: Artificial Sequence
<220> FEATURE:
<223> OTHER INFORMATION: synthetic excision site sequence

<400> SEQUENCE: 55
tgttggactt gaattg                                                   16

<210> SEQ ID NO 56
<211> LENGTH: 12
<212> TYPE: DNA
<213> ORGANISM: Artificial Sequence
<220> FEATURE:
<223> OTHER INFORMATION: synthetic excision site sequence

<400> SEQUENCE: 56
ggacttgaat tg                                                       12

<210> SEQ ID NO 57
<211> LENGTH: 16
<212> TYPE: DNA
<213> ORGANISM: Artificial Sequence
<220> FEATURE:
<223> OTHER INFORMATION: synthetic excision site sequence

<400> SEQUENCE: 57
gggtctactt gaattg                                                   16

<210> SEQ ID NO 58
<211> LENGTH: 10
<212> TYPE: DNA
<213> ORGANISM: Artificial Sequence
<220> FEATURE:
<223> OTHER INFORMATION: synthetic excision site sequence

<400> SEQUENCE: 58
```

-continued

```
<210> SEQ ID NO 59
<211> LENGTH: 10
<212> TYPE: DNA
<213> ORGANISM: Artificial Sequence
<220> FEATURE:
<223> OTHER INFORMATION: synthetic excision site sequence

<400> SEQUENCE: 59
acttgaattg                                                              10

<210> SEQ ID NO 60
<211> LENGTH: 13
<212> TYPE: DNA
<213> ORGANISM: Artificial Sequence
<220> FEATURE:
<223> OTHER INFORMATION: synthetic excision site sequence

<400> SEQUENCE: 60
cgagttggtt gga                                                          13

<210> SEQ ID NO 61
<211> LENGTH: 11
<212> TYPE: DNA
<213> ORGANISM: Artificial Sequence
<220> FEATURE:
<223> OTHER INFORMATION: synthetic excision site sequence

<400> SEQUENCE: 61
cgagttggtt g                                                            11

<210> SEQ ID NO 62
<211> LENGTH: 14
<212> TYPE: DNA
<213> ORGANISM: Artificial Sequence
<220> FEATURE:
<223> OTHER INFORMATION: synthetic excision site sequence

<400> SEQUENCE: 62
ttagacttga attg                                                         14
```

TRANSPOSON VECTOR FOR VERTEBRATE AND INVERTEBRATE GENETIC MANIPULATION

CROSS-REFERENCE TO RELATED APPLICATIONS

This application claims priority benefit of U.S. provisional application No. 62/081,947, filed Nov. 19, 2014, which application is herein incorporated by reference.

BACKGROUND OF THE INVENTION

Transposons are valuable agents for genetic manipulation and can be used in any number of gene transfer applications, including gene therapy. DNA transposons move by a cut and paste mechanism in which a transposase gene, encoded by the transposon, is transcribed and translated into a transposase protein. Transposase binds to the ends of the transposon, usually within and around the terminal inverted repeats (TIRs). The transposon is then excised from one genomic location and integrates into another genomic location.

There are very few transposons that have been characterizes that exhibit a high levels of activity in mammalian cells. Accordingly, there is a need for additional transposons that can be used for genetic manipulation of mammalian cells. This invention addresses that need.

BRIEF SUMMARY OF THE INVENTION

The invention is based, in part, on the discovery of a transposable element from the mosquito *Aedes aegypti*. Thus transposon, referred to herein as Muta1, catalyzes its own transposition and is the first member of the Mutator superfamily with demonstrated activity in a transgenic organism. Specifically, it is highly mobile in *Saccharomyces cerevisiae* (yeast), *Drosophila melanogaster* and *A. aegypti* embryos and in other vertebrate and invertebrate cells, including mammalian cells.

In one aspect, the invention provides an isolated Muta1 nucleic acid comprising a polynucleotide encoding a Muta1 transposase having at least 70% identity to SEQ ID NO:2. In some embodiments, the Muta1 transposase has at least 85% or at least 90% identity to SEQ ID NO:2. In some embodiments the Muta1 transposase comprises SEQ ID NO:2.

In a further aspect, the invention provides an expression vector and recombinant host cells comprising a Muta1 nucleic acid of the invention as described herein.

In an additional aspect, the invention provides an isolated nucleic acid comprising a Muta1 transposon, wherein the Muta1 transposon comprises a 5' inverted terminal repeat having at least 70% identity to SEQ ID NO:3 and a 3' inverted terminal repeat having at least 70% identity to SEQ ID NO:4, wherein the 5' and 3' inverted terminal repeat flank a nucleic acid sequence to be inserted into a target polynucleotide. In some embodiments, the 5' inverted terminal repeat comprises SEQ ID NO:3 and the 3' terminal repeated comprises SEQ ID NO:4. In some embodiments, the nucleic acid sequence to be inserted into a target polynucleotide is a marker gene, optionally a fluorescent protein. In some embodiments, the invention provides vector comprising the isolated nucleic acid a Muta1 transposon of the invention.

In a further aspect, the invention provides a gene transfer system comprising: a nucleic acid encoding comprising a polynucleotide encoding a Muta1 transposase having at least 70% identity to SEQ ID NO:2; and a nucleic acid comprising a Muta1 transposon, wherein the Muta1 transposon comprises a 5' inverted terminal repeat having at least 70% identity to SEQ ID NO:3 and a 3' inverted terminal repeat having at least 70% identity to SEQ ID NO:4, wherein the 5' and 3' inverted terminal repeat flank a nucleic acid sequence to be inserted into a target polynucleotide. In some embodiments of the gene transfer system, the Muta1 transposase has at least 85% identity, or at least 90% or 95% identity, to SEQ ID NO:2. In some embodiments, the Muta1 transposase comprises SEQ ID NO:2. In some embodiments of the gene transfer system, the Muta1 transposon 5' inverted terminal repeat comprises SEQ ID NO:3 and the 3' terminal repeated comprises SEQ ID NO:4. In some embodiments of the gene transfer system the polynucleotide encoding the Muta1 transposase and the nucleic acid comprising the Muta1 transposon or present on separate vectors.

In further aspects, the invention provides a method of introducing a nucleic acid sequence of interest into a target polynucleotide, the method comprising introducing a Muta1 transposon into a host cell that comprises a Muta1 transposase as described herein, wherein the Muta1 transposon comprises a 5' inverted terminal repeat having at least 70% identity to SEQ ID NO:3 and a 3' inverted terminal repeat having at least 70% identity to SEQ ID NO:4, wherein the 5' and 3' inverted terminal repeat flank a nucleic acid sequence to be inserted into a target polynucleotide. In some embodiments, the 5' inverted terminal repeat comprises SEQ ID NO:3 and the 3' terminal repeated comprises SEQ ID NO:4. In some embodiments, the host cell is a vertebrate host cell, e.g., a mammalian cell. In some embodiments, the mammalian cell is a

BRIEF DESCRIPTION OF THE DRAWINGS

FIG. 1A-1C excision footprints (FIG. 1A: AAAATCGGAC (SEQ ID NO:37), AAAATCGGACGGGTCTA (SEQ ID NO:38), AAAATCGGACGGGTCTACCCCGT (SEQ ID NO:39), GGTAGTCCCATCAAGT (SEQ ID NO:40); FIG. 1B: GGACTTCAATAG (SEQ ID NO 41), TTCAATAGATCA (SEQ ID NO:42); FIG. 1C: GGACGCTTGAACT (SEQ ID NO:43), GCTTCAACTATCA (SEQ ID NO:44)); FIG. 1D-1F, excision events FIG. 2 provides illustrative data for excision of Muta1 from human chromosomes.

DETAILED DESCRIPTION OF THE INVENTION

Figure 1:
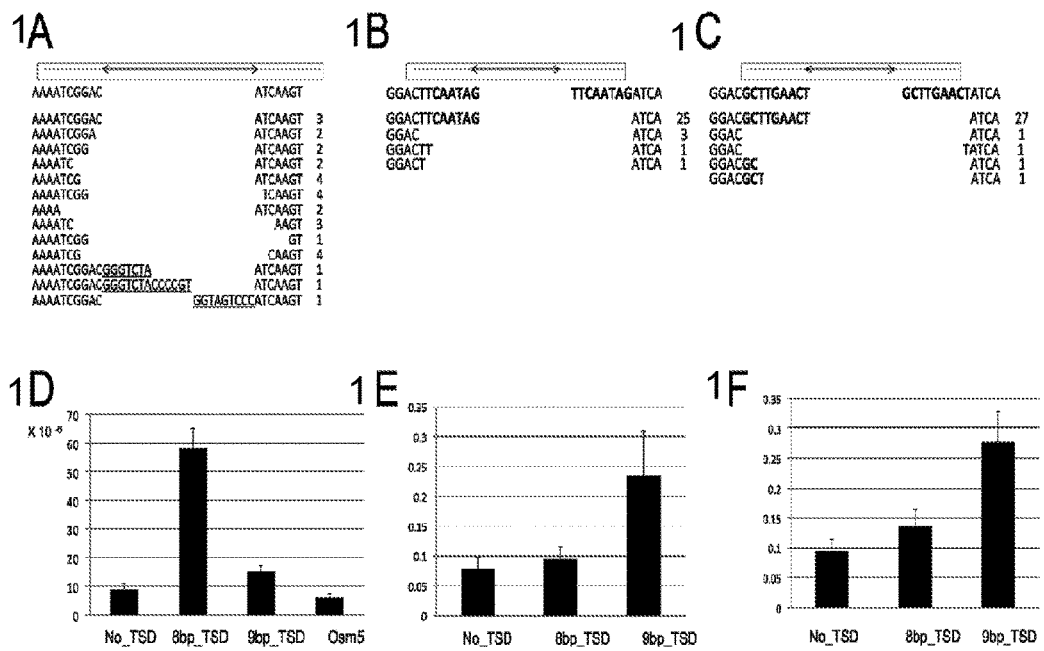
FIG. 1A-F provides data illustrating the transposition activity in yeast and shows excision events and footprints.

As used herein, a "Muta1 transposon" or "Muta1 transposable element" are used interchangeably to refer to a nucleotide sequence that has left and right transposon termini containing the 5' and 3' terminal inverted repeats recognized by a Muta1 transposase that flank an insert, for example a nucleic acid that is to be inserted into a target genome or encodes a selectable or phenotypic marker. By "recognized" is meant that a Muta1 transposase is capable of binding to the inverted repeat and then integrating the transposon flanked by the inverted repeat into the genome of a target cell.

As used herein, the term "transposase" refers to a polypeptide that catalyzes the excision of a transposon from a donor polynucleotide and the subsequent integration of the transposon into the genomic or extrachromosomal DNA of a target cell. A "cognate" transposase, as referred to herein, is a transposase which is effective to activate transposition of a given transposon, including excision of the transposon from a first integration site and/or integration of the transposon at a second integration site. Thus, a Muta1 transposase having the sequence of SEQ ID NO:2 is a cognate transposase for the Muta1 transposon. The term also encompasses functional variants of the transposase of SEQ ID NO:2 where the variant can activate transposition of a Muta1 transposon.

As used herein, the term "Muta1 transposase" refers to a transposase in the Mutator superfamily of transposases that catalyzes the excision of a transposon having the terminal repeats set forth in SEQ ID NO:3 and SEQ ID NO:4 and integration into a target DNA. The term encompasses functional variants of the specific polypeptides described herein. A nucleic acid that encodes a Muta1 transposase refers to a gene, pre-mRNA, mRNA, and the like, including nucleic acids encoding of the particular amino acid sequences described herein. In embodiments, an a Muta1 transposase gene encodes a polypeptide having an amino acid sequence that has at least 70%, 75%, 80%, 85%, 90%, preferably 91%, 92%, 93%, 94%, 95%, 96%, 97%, 98% or 99% or greater, amino acid sequence identity, preferably over a region of at least about 25, 50, 100, 200 or more amino acids, or over the length of the entire polypeptide, to an amino acid sequence of SEQ ID NO:2. In some embodiments, a Muta1 transposase has at least 70%, 75%, 80%, 85%, 90%, preferably 91%, 92%, 93%, 94%, 95%, 96%, 97%, 98% or 99% or greater, amino acid sequence identity to SEQ ID NO:2. The DDE motif that is characteristic of the DDE domain is located at residues D214, D283 and E419 of the Muta1 transposase polypeptide sequence shown in SEQ ID NO:2.

A "Muta1 transposon system" as used herein refers to a Muta1 transposon and cognate transposase.

The term "transposition reaction" as used herein, refers to a reaction whereby a transposase forms a complex with a transposon end and a target DNA sequence, introduces a break in the target DNA, and catalyzes the transfer of the transposon end to the target DNA.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 50% sequence identity with a reference sequence. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a Muta1 transposase polypeptide may be at least 70%, 75%, 80%, 85%, 90%, 91%, 92%, 93%, 94%, 95%, 96%, 97%, 98%, or 99% identical to SEQ ID NO:2.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. Similarly, a "recombinant protein" is a protein made using recombinant techniques, i.e., through the expression of a recombinant nucleic acid as depicted above. The term also encompasses the progeny of a cell that is subjected to the initial genetic manipulation.

A polynucleotide is "heterologous" to an organism or a second polynucleotide or polypeptide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence.

As used herein, the term "isolated" means that naturally accompanying material is at least reduced, or preferably substantially completely eliminated, in normal circumstances. Therefore, the term "isolated cell" refers to a cell substantially free from other accompanying substances (e.g., other cells, proteins, nucleic acids, etc.) in natural circumstances. The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are chemically synthesized. Isolated nucleic acids are preferably free from sequences naturally flanking the nucleic acid within an organism from which the nucleic acid is derived (i.e., sequences positioned at the 5' terminus and the 3' terminus of the nucleic acid).

The term "a" and "an" and "the" as used to describe the invention, should be construed to cover both the singular and the plural, unless explicitly indicated otherwise, or clearly contradicted by context.

INTRODUCTION

This invention is based, in part, on the discovery of a new transposon and cognate transposase.

This invention relies in part on routine techniques in the field of recombinant genetics, e.g., for methods of expressing a Muta1 transposase and methods of generating a Muta1 transposon that comprises a nucleic acid sequence of interest to be introduced into a target polynucleotide. Basic texts disclosing the general methods of use in this invention include Sambrook & Russell, Molecular Cloning, A Laboratory Manual (3rd Ed, 2001); and Current Protocols in Molecular Biology, Ausubel, 1994-2009, including supplemental updates through 2012).

Transposon

A Muta1 transposon in accordance with the present invention comprises a region that has an insert that is flanked by an inverted terminal repeat (ITR) at the 5' and 3' ends that are recognized by the Muta1 transposase. The ITR at the 5' end of the Muta1 transposon is: GGGTCTACCCCGTTTG-GCATAATGCCGTTTGGCATAATGCCGTTTGGCATA-CAGTCG TTTGGCATAAAGTCGTTTGGCATAATAGT-CATTTGGCATAACAGTCGTTTGGCATAA TGGTCATTTGGCATAATGGTCGTTTGGCATAA (SEQ ID NO:3), or a functional variant thereof. The 146 bp ITR at the 3' end of the Muta1 transposon is: TTATGCCAAAC-GACTATTATGCCAAATGACCATTATGCCAAATGACT-ATTATGCCAA ATGGCATTATGCCAAACGACTATTAT-GCCAAACGACTGTATGCCAAACGGCATTATG CCAAACGGCATTATGCCAAACGGGGTAGACCC (SEQ ID NO:4), or a functional variant thereof.

A functional variant of a Muta1 ITR is a variant of SEQ ID NO:3 or SEQ ID NO:4 that retains the ability to mediate transposition by a Muta1 transposase. In some embodiments, a Muta1 ITR variant comprises at least 25, at least 50, at least 75, at 100, at least 110, at least 120, at least 130, or at least 140 contiguous nucleotides of SEQ ID NO:3 or SEQ ID NO:4. In some embodiments, a Muta1 ITR variant in accordance with the invention is at least 60%, often at least 65%, at least 70%, at least 75%, at least 80%, at least 85%, at least 90%, at least 95%, at lease 96%, at least 97%, at least 98%, or at least 99%, or greater identical to SEQ ID NO:3 or SEQ ID NO:4 over a region of at least 100 or 120 nucleotides, or greater, or over the full-length of SEQ ID NO:3 or SEQ ID NO:4.

The transposon for use in the invention comprises an insert that is to be transferred to a target polynucleotide, e.g., a target genome. The insert is often at least 250 base pairs, at least 500 base pairs, at least 1 kb, or at least 1.5 kb in length. In other embodiments, the transposon comprises an insert of at least 2 kb, at least 2.5 kb, at least 3 kb, at least 4 kb, at least 5 kb, at least 6 kb, at least 7 kb, at least 8 kb, at least 9 kb, at least 10 kb, at least 11 kb, at least 11.5 kb, at least 13 kb, at least 14 kb, or at least 15 kb. In some embodiments, the transposon comprises an insert no greater than 20 kb or no greater than 35 kb in length. In some embodiments, the insert is 15 kb or less, e.g., from 250 base pairs to 15 kb in length.

Transposase

The invention additionally provides a Muta1 transposase having a sequence set forth in SEQ ID NO:2, or a functional variant thereof. In some embodiments, the variant has at least 60%, at least 65%, at least 70%, at least 75%, at least 80%, at least 85%, at least 90%, at least 95%, or greater, sequence identity to SEQ ID NO:2. In some embodiments, the transposase comprises the amino acid sequence of SEQ ID NO:2.

The structure of transposases in various superfamilies has been characterized. All transposases have a DDE/D triad that catalyzes the "cut and paste" transposition reaction. The DDE/D motif has two aspartic acid (D) residues and a glutamic acid (E) residue, or a third D, located in a conserved core that forms a characteristic RNase H-like fold of mixed α-helices and β-strands (β1-β2-β3-α1-β4-α2/3-β5-α4-α5/6) (see, e.g., Hickman, et al., *Crit Rev Biochem Mol Biol* 45:50-69, 2010 for a review). The first D is located on β1, the second D is on or just after β4, and the third D/E appears on or just before α4 (11).

Additional amino acid residues and motifs that are highly conserved among superfamily members have also been described (see, e.g., Yuan & Wessler, *Proc. Natl. Acad Sci USA*, Apr. 25, 2011, which is herein incorporated by reference). Muta1 transposase is a member of the Mutator superfamily group of transposases. Thus, a functional variant of a Muta1 transposase of SEQ ID NO:2 typically comprises sequences that are characteristic of that superfmaily. For example, the Mutator superfamily has a C(2)H, (CxxH) motif at a position 15 to 45 amino acids downstream from the second D of the DDE triad. Furthermore, additional highly conserved amino acid residues or motifs within the DDE/D domain are present that together form a "signature string" that is specific to each superfamily. The DDE motif that is characteristic of the DDE domain is located at residues D214, D283 and E419 of the Muta1 transposase polypeptide sequence of SEQ ID NO:2. One of skill can identify functional variants based on these known structural features of transposases. For example, one of skill can obtain a variant by using the sequence alignments of Mutator transposases to identify residues within conserved sequences that would be expected to retain transposase function as well as residues outside of the conserved regions that would be expected to be tolerant to substitution.

Activity of a transposase can be determined using known assays, such as those employed in the EXAMPLES section for evaluating Muta1 activity. Assays for measuring the excision of a transposon from a vector, the integration of a transposon into the genomic or extrachromosomal DNA of a cell, and the ability of transposase to bind to an inverted repeat are known to the art (see, for instance, (Ivies et al. Cell, 91, 501-510 (1997); WO 98/40510 (Hackett et al.); WO 99/25817 (Hackett et al.), WO 00/68399 (McIvor et al.), incorporated by reference in their entireties herein. For purposes of determining the frequency of transposition of a transposon of the present invention, the activity of the baseline transposon is normalized to 100%, and the relative activity of the transposon of the present invention determined. Preferably, a transposon of the present invention transposes at a frequency that is at least about 50% of that of the Muta1 transposon illustrated in the Examples section. Thus, a Muta1 variant may A Muta1 transposase specifically binds to the ITR of a Muta1 transposon. Specific binding generally refers to a molecule that binds to a target with a relatively high affinity compared to non-targets. One feature that distinguishes transposases from each other is that they do not specifically bind to transposons recognized by other transposases. Thus, a Muta1 transposase typically binds to the ITR of a Muta1 transposon with at least twice, typically at least five times, or greater affinity compared to binding to the ITR of another Mutator transposon, or to the ITR of a transposon from a different superfamily.

Configurations of Transposase Systems

Methods of introducing a sequence of interest into a target nucleic acid using a Muta1 transposon system of the invention are well known. In some embodiments, the method comprises using two vectors. In such a method, one of the vectors comprises the transposon, comprising the nucleic acid sequence of interest inserted between the ITRs, into which is inserted a nucleic acid sequence of interest, and a second vector that comprises a nucleic acid sequence encoding a Muta1 transposase. In typical embodiments, the gene is not flanked by the terminal inverted repeats and so cannot be mobilized by the transposase. An advantage of this system configuration is that, following introduction into the cell, the vectors are ultimately degraded meaning that the transposon has only a short time period during which it transposes into the genome. One of skill understands that when introducing the components into a cell, the vectors may be delivered concurrently or sequentially. When delivered concurrently, the vectors may be formulated in the same mixture or as separate mixtures. In some embodiments, a vector comprising a Muta1 transposon may be introduced into a cell the stably expresses a Muta1 transposase, e.g., under the control of an inducible promoter.

In other embodiments, the transposon and transposase gene may be introduced into a cell using a single vector comprising the transposon (that comprises the gene of interest flanked by ITRs) where the transposase gene is present on the vector located as a separate coding transcribed region. In such embodiments, the vectors are typically designed such that only the transposon transposes, leaving the rest of the vector, including the transposase gene. In such embodiments, the transposase-encoding region is present outside of the inverted repeats that flanking the inserted nucleic acid. In some embodiments, the whole vector can integrate in a transposase-independent manner into a target nucleic acid.

As explained herein, in a Muta1 transposon system of the invention, a Muta1 transposase recognizes inverted repeats that flank an insertion nucleic acid, which nucleic acid is to be inserted into a target polynucleotide, such as the genome of a target cell. The invention may employ a wide variety of nucleic acid inserts, which may be sequences that are endogenous or exogenous relative to the target polynucleotide.

In some embodiments, a Muta1 transposon comprises a nucleic acid insert that encodes a protein of interest. In some embodiments, the nucleic acid insert additionally comprises regulatory elements to which the coding sequence is operably linked. Examples of regulatory elements include, but are not limited to promoters, enhancers, termination signals, polyadenylation signals, and splicing sequences. A Muta1 transposon may additionally comprise a polynucleotide encoding a selectable marker.

A wide variety of vectors for introducing a Muta1 transposon or transposase into a target polynucleotide of interest are known in the art. Such vectors include, but are not limited to, plasmid vectors; viral vectors, such as retroviral vectors, e.g., lentiviral vectors; adenoviral vectors; pox viral vectors; adeno-associated viral vectors; herpes viral vectors, and the like. In some embodiments, the vector is a plasmid vector. The vectors can be introduced into a cell using any known methodology, including, but not limited to injection, electroporation, transfection, lipofection, viral infection, and ballistic methods.

A Muta1 transposon system of the invention can be used in any number of cells from different organisms including both unicellular, e.g., yeast, and multi-cellular organisms. Multicellular organisms of interest include plants as well as animals, e.g., vertebrates. In some embodiments, a Muta1 transposon system is introduced into an avian cell, e.g., a chicken cell. In some embodiments, a Muta1 transposon system is introduced into a mammalian cell, such as a rodent cell, or a bovine, porcine, equine, ovine, canine, feline, cell. In some embodiments, a Muta1 transposon system is introduced into a primate cell, such as a non-human primate or human cell. In some embodiments, the cell can be from a desired tissue, e.g., skeletal or cardiac muscle cells, neural cells, hepatocytes, or a desired type, such as a fibroblast or epidermal cell. In some embodiments, the cell may be an embryonic stem cell, e.g., a human embryonic stem cell, or a pluripotent stem cell, such as a hematologic stem cell. A Muta1 transposon system can be introduced into a cell either in vitro or in vivo. In some embodiments, a Muta1 transposon system may be introduced into cell ex vivo. Cells that are selected that have the desired genetic modification, e.g., express a transgene of interest that is introduced using the transposon system, may subsequently be re-introduced into the host.

Uses of a Muta1 Transposon System

A Muta1 transposon system in accordance with the invention can be used in any application for which transposons and transposases are used. Examples of uses are described by Belay, et al. *Stem Cells* 28, 1760-1771, 2010; Claeys Bouuaert & Chalmers, *Genetica* 138, 473-484, 2010; Ding, et al. Cell 122, 2005; Dupuy et al. Nature 436: 221-226, 2005; Dupuy et al., *Human Molecular Genetics* 15, R75-R79, 2006; Grabundzij a et al., *Molecular Therapy* 18, 1200-1209, 2010; Ivies & Izsvak, *Current Gene Therapy* 6, 593-607, 2006; Ivies et al., *Nature Methods* 6, 415-422, 2009; Largaespada, *Methods Mol Biol* 530, 379-390, 2009; Li et al., *Nucleic Acids Res* 39, e148, 2011; Li et al., *Proc Natl Acad, Sci USA,* 2012; Venken & Bellen. (2007). Wilson et al., *Molecular Therapy* 15, 139-145, 2007; Wu et al., *Proc Natl Acad Sci USA* 103, 15008-15013, 2006; and Yusa, et al., *Proc Natl Acad, Sci USA* 108, 1531-1536, 2011. The following are illustrative of uses of a Muta1 transposon system.

In one embodiment, a Muta1 transposon system is used to introduce transgenes into genome to make transgenic cells. Thus, for example, stable new genetic lines can be generated. The gene of interest that is introduced into a nucleic acid present in a cell can be any gene, such as a desired protein encoding gene.

In some embodiments, Muta1 transposon system can be employed as a mutagen to identify genes and enhancers. For example, in some embodiments a transposon is employed in an enhancer trap. In an enhancer trap, a genetic marker, such as a gene encoding fluorescent protein or a gene encoding a protein the presence of which can be detected by staining or by catalytic assays, is placed under the control of a weak promoter, and this promoter-gene is placed within a transposon. Should this transpose insert near a strong promoter or enhancer then the genetic marker will show the same temporal- and tissue-specific expression as the genes normally regulated by this promoter or enhancer. These genes can then be positionally cloned and identified using the transposon inserted nearby. Similarly, in a gene trap, the methodology is similar except that an intron acceptor splice site precedes the genetic marker. Insertion of the transposon downstream of a donor splice site in a gene leads to the expression of the genetic marker in those tissues in which the gene is normally expressed. Once again this gene can be positionally cloned using the transposon inserted nearby. In other uses, a Muta1 transposon system can be used in a "jumpstarter" strain in which a transposon is used to generate one transgenic strain and the transposase gene is inserted into another strain using an unrelated transposable element. These two strains are then crossed so that the transposase gene and the transposon are present in the same genome enabling the genetically marked transposon to be remobilized. Backcrossing then removes the transposase gene leaving the remobilized transposons in new genomic locations.

In some embodiments, a Muta1 transposon system of the invention can be used to engineer cells by introducing recombinase systems into a desired cell that can then be used for subsequent genome manipulations. For example, a Muta1 transposon system can be used to introduce site-specific recombinases and the small target sequences they recognize into an organism.

The present invention further provides an efficient method for producing transgenic organisms, e.g., transgenic animals. For example, transgenic animals generated using a transposon system of the invention may contain a nucleic acid sequence inserted into the genome of the animal that expresses a desired protein, such as a protein that is produced in milk, urine, blood or eggs.

A Muta1 transposon system of the invention also finds use in therapeutic applications, such as gene therapy applications. The transposon system may be used to deliver a wide variety of therapeutic nucleic acids, including nucleic acids that encode a protein deficient in various metabolic or immune defects or nucleic acids used for cancer therapies.

In certain preferred embodiments, a Muta1 transposon that encodes one or more reprogramming factors, such as Sox, Oct, Nanog, Klf4, or c-Myc may be used to generated pluripotent stem cells that can be used for a variety of therapeutic purposes.

The present invention also provides kits comprising a Muta1 transposase, or a nucleic acid encoding a Muta1 transposase; and/or a Muta1 transposon that can be used to transfer a nucleic acid sequence of interest into a target polynucleotide The following examples are offered to illustrate, but not to limit, the claimed invention.

EXAMPLES

Example 1. Identification of Muta1 Transposon

An algorithm that identifies candidate active DNA transposons in genome sequence was applied to the sequenced *A. aegypti* genome (Han, et al., *Nucl. Acids Res.* 37(11):e78, 2009). Eight copies of a Mutator-like transposon were detected that were all full length and flanked by different target site duplications (TSDs). Copies 1 through 7 were identical: they all encoded a transposase of 504 amino acids. Copy 8 had 2 point mutations relative to Copies 1 through 7, and encoded a truncated transposase of 475 amino acids matching the wild type transposase from position 1-221 and 251-504.

The full length Copy 1 was cloned from the genome of the Liverpool strain of *A. aegypti* using PCR and DNA primers designed from sequences flanking and within the transposon. Copy 1 (renamed Muta1) is 3198 bp and contains 146 bp imperfect terminal inverted repeats (TIRs). The coding sequence for the 504 amino acid transposase commences at position 1334 and ends at 2910, with an intron located at positions 2475 through 1536.

The full nucleic acid sequence of Muta1 is:

(SEQ ID NO: 1)

```
GGGTCTACCCCGTTTGGCATAATGCCGTTTGGCATAATGCCGTTTGGCATACAGTCG
TTTGGCATAAAGTCGTTTGGCATAATAGTCATTTGGCATAACAGTCGTTTGGCATAA
TGGTCATTTGGCATAATGGTCGTTTGGCATAATTTGAAAAGAAGCTTTAGATTAAAT
AATAAAAAACAAAACATATACATGATGAACATCTTTATCTAGTCGTACGCTTCTCAC
ACTGTTATGGGTCACTTTGTCACGATCCATTAGTCACTGTTTTTCAAATGTATTTCAA
ATGAAAATGCCTTATACTAGTTTATTTGATATTTGTACTACGAAGCTGGAAATGTTTT
AACGAATAACTTGTCATGATAAATAATAATTACACAAGTCTCAGTTTAATCATGGGA
TGAATTGGTTGAGTATGCGGATAACGTGATCTAAAAAATAAGAAGTTTGTTTTATTT
TATTTATGTTTTATTAGCCAATGATTTCTCTATTTTTTGCAGTACCATTCAAGTATTC
AATTCGCTTATGACTCATACAATATGCATAATACCGATTCTGTGTTGTTGCTAGACA
ATAATACTTGAAAAGTGAGAATATTTCGTTTCGGTATCTTTCAAAACTATTTCCTTTA
ACATCAACAATAAAGTTCATCCACTCTGAAGCGTCTTGTAATCCATTCACGTACAAA
AATGTTGTCAATTTAAGTCGCTCTTGATATTTCAATGTCTTGGATGCGATTATTTTTT
GATATTAGAAGGCCATAAATAAACTGGTCCACAGACGTCTTGGAACGTAAATAGTG
GATTCGTTATATCTTCATATTCACGGTAAACTTTACACATTTTGTTTAAAGGATTGTT
CATTTTGTTAACTTTAAAAACACTTCAATTTATTTAATATACAAATAAGCCAAATTAA
TTAAAACTTTTAGCGATAAAATCACTCGGCAGACATGCGTACGTAAAACTGTTACAA
TTTTATTCGAACATGCCTCGTCCAACACCTGTAATGCCCGTAAATGCATGTCAGTCCC
ATGTTTGCTGGATTTCCTATTCACATGGGACAATTATGCATTTATGCTCAGTGTACCT
ACCTCATGCTTAGGAATTCAAATAGAACGCAGCTTGCTGTGATCCAATTGAATTTAA
AAGTCACCCATTGGTCGAAAAATCGAAAAATTTAAAATATGATCAGTAGGCTGTGA
CCACGTTGTACCCCGTTGATACTGGTTGCTAAGTAACGAGGCCGGTATCATTGTAAG
AGGCATACTAGTGGAAGTTGGAGAAAGGGTTCTTTTCTGATTCTGCTGTACGGCGGT
TTAGACGCGAAAAATGGACTCGGACAGCGATAGCGATTTTTACGGAGTGGATGCAG
CCGAAGCGGAAAATGATGTGCCGAAAGTGCTTAAATCATCCAGAGGAAAGGATTGT
TTGGCTTTCAAAGGATTTTTATTCTATTCAAACAGAACACCGGTAAGTTTTTTTTAA
ATTGTGCGAAATAATAATACAACTAAAAACCAAATTAATGTTTTAGAATGGTCCCAC
CCACTACTGGGAATGTAGGGGTAGACCACATGGACGCGGCTCGGGAAGCAGATGCT
CTGCGCGTATGGTAACGTTCAAGGCGGGGAACGAACACCGCGTTCTGTCATGTTCGG
ACCATAACCACGAAAGCGACCCAATTCATTTAATGGGCTAATGATGAGGAGTTCC
CTAAAGCGACGGGCCAACCAAAACAATGCAACGCCAGCGAAAATAGTACGCCAAG
CCGGAGCAGAATTTTCTAATGCGGTGCAGCAGAGGATGTCGTTAAATGCACAACGT
AAAATCATCGACCGAGTGCGAAAAAGTGACGAACTCCCAAAGGAACCCACTTCGTT
GGCCGAATTTGAGGTGCCGATCAGCTTAAGGACAACCGTCGATGGAGAATCTTTCCT
TATGTCTGATATTAAGGAAGGAAGCGACAGAGCAATCATTTTTGGTACGCTGGAAG
GATTACGACGTTTAGCCCTTGCCAAATACTGGATCGTTGACGGAACGTTCGATTGCG
TTCCAGGTTTGTTTCGGCAACTGTTCACCATTCTTGGTAGCAGTTCGCCAAACCACGA
ACATGCGTTCCCCATAATACACACGTTGATGACAGCAAAAAATGAAGCGCTGTATC
GGGCAGTCTTTGCAACGCTAATAGAAAAGGCAAATGAGCTGGGGATCGATCTAGAT
```

-continued

```
CCACCAGTCATTTTATCAGATTTTGAAAAGGCTATCATCAACGCTATAAAATCTGAG

TTCCCAGAAACAAAGCAAAATGCGTGCTTCTTTCACCTGTCCCAGAATTTCTGGAAA

AGAATTCAAGAGGCAAAGCTTATTGGAGAAATGACCAACAATATCGCCCTGTATCA

TTTCTTCAAAAAGACGCAAGCCCTTGCTTTTTTACCAACTGAACGTATACCAGCCGC

GTTTGAGAATTTGAAAAAAAATGCGCCTGTTCAACTGAAGGATTTTATATCTTATGT

GGACGAATACTACATTATGGGTCGTGTCCGGCGTATCGGAAAGGATGGGCGAATCG

TTCGTACAGAACCACTGTACCCGCCGTCGTTGTGGTCGATTTATGACAACGTTTTGTC

AAACGTTCCGCGTACCACAAACCAGATTGAAGCCTGGCACCGACGTTGGCAAACAC

TGGTAGCACGTCAAACTGGAGTGATCAAGCTGATGGGTGAGTTAAGGCTGGAGGAA

AAATATACGGTTGGACAAATCGCAGCTCTTCTGGCTGGTACGTCCAGCAAGCAGAA

GAAGACGATGCATCAAATTAATGATCAAGCGGTGAAGAATATTGTTGAAAATATTG

ATAAATATCAGGAAACTGATTATCTTGAGGCAATTGCAGCTCACTTAGGATCAAAAT

CAAAATAAGAGAGAGGTTTTTCATTACATTTCTATGTATACATAACAAAAATTGAAA

TAATAAATGAATTGGTAAATATATATTTCTTTTCATTGACTCATGTGAACAACGGTA

ACAAAAATGTTTTAAAAATACGATTTCTGGTTATGGTTATGCCAAACGACTATTATG

CCAAATGACCATTATGCCAAATGACTATTATGCCAAATGGCATTATGCCAAACGACT

ATTATGCCAAACGACTGTATGCCAAACGGCATTATGCCAAACGGCATTATGCCAAAC

GGGGTAGACCC
```

The amino acid sequence of the 504 amino acid Muta1 transposase is:

```
                                                  (SEQ ID NO: 2)
MDSDSDSDFYGVDAAEAENDVPKVLKSSRGKDCLAFKGFLFYSNRTPNGP

THYWECRGRPHGRGSGSRCSARMVTFKAGNEHRVLSCSDHNHESDPIHLM

GLMMRSSLKRRANQNNATPAKIVRQAGAEFSNAVQQRMSLNAQRKIIDRV

RKSDELPKEPTSLAEFEVPISLRTTVDGESFLMSDIKEGSDRAIIFGTLE

GLRRLALAKYWIVDGTFDCVPGLFRQLFTILGSSSPNHEHAFPIIHTLMT

AKNEALYRAVFATLIEKANELGIDLDPPVILSDFEKAIINAIKSEFPETK

QNACFFHLSQNFWKRIQEAKLIGEMTNNIALYHFFKKTQALAFLPTERIP

AAFENLKKNAPVQLKDFISYVDEYYIMGRVRRIGKDGRIVRTEPLYPPSL

WSIYDNVLSNVPRTTNQIEAWHRRWQTLVARQTGVIKLMGELRLEEKYTV

GQIAALLAGTSSKQKKTMHQINDQAVKNIVENIDKYQETDYLEAIAAHLG

SKSK.
```

The 146 bp ITR at the left end of the Muta1 transposon is:

```
                                                  (SEQ ID NO: 3)
GGGTCTACCCCGTTTGGCATAATGCCGTTTGGCATAATGCCGTTTGGCAT

ACAGTCGTTTGGCATAAAGTCGTTTGGCATAATAGTCATTTGGCATAACA

GTCGTTTGGCATAATGGTCATTTGGCATAATGGTCGTTTGGCATAA.
```

The 146 bp ITR at the right end of the Muta1 transposon is:

```
                                                  (SEQ ID NO: 4)
TTATGCCAAACGACTATTATGCCAAATGACCATTATGCCAAATGACTATT

ATGCCAAATGGCATTATGCCAAACGACTATTATGCCAAACGACTGTATGC

CAAACGGCATTATGCCAAACGGCATTATGCCAAACGGGGTAGACCC.
```

The 8 bp TSD flanking Muta1 in the *A. aegypti* genome is GCTTCAAATG (SEQ ID NO:34) at the left end and GCTTCAAATG (SEQ ID NO:34) at the right end.

Example 2. Muta1 is Highly Active in Yeast Cells

Cloning of the Muta1 Element and Construction of Yeast Expression Vector.

Muta1 was amplified from *A. aegypti* DNA using flanking primers Mu1F, 5'-TCTGGAGGGTTGATTGTTTG-3' (SEQ ID NO:5), and Mu1R, 5'-CTGAAGGTGGTCCGTCTTAC-3' (SEQ ID NO:6), then cloned into Zero Blunt® TOPO vector (Invitrogen). Exon1 was amplified using primer MuOPL, 5'-CACCATGGACTCGGACAGCGAT-3' (SEQ ID NO:7), and MuE1R, 5'-CAGTAGTGGGTGGGACCAT-TCGGTGTTCTGTTTGAATAGA-3' (SEQ ID NO:8); exon 2 was amplified using primers MuOR, 5'-TTATTTT-GATTTTGATCCTAAGTGA-3' (SEQ ID NO:9), and MuE2L, 5'-CAGTAGTGGGTGGGACCATTCGGTGT-TCTGTTTGAATAGA-3' (SEQ ID NO:10). Overlapping PCR of the purified DNA fragment of the two exons was performed using primers MuOPL and MuOR to obtain the complete coding sequence, which was then cloned into pENTR™/D-TOPO® vector (Invitrogen) and transferred into expression vector PAG415GAL-ccdB by gateway recombination.

Construction of Yeast Reporter Vectors.

A nonautonomous element nMuta1 was used to assay the transposition activity of Muta1 (FIG. 1A-F). The nMuta1 element with flanking sequences was amplified using primer nonMuF, 5'-TGGAGAAGGGTATGGAGGA-3' (SEQ ID NO:11), and nonMuR, 5'-GGCAGGACGGACATTTATT-3' (SEQ ID NO:9). A second round PCR was performed to add different lengths of TSD to the element. An 8b (TTCAATAG), a 9 bp (GCTTGAACT) and no TSD version were amplified by PCR using the primers

```
MuTA8bp_5IN (5' to 3'):
                                    (SEQ ID NO: 13)
TAACAATCAAGAAAAACAAGAAAATCGGACTTCAAATGGGGTCTACCCCG

TTTGGC
and

MuTA8bp_3IN (5' to 3'):
                                    (SEQ ID NO: 14)
CAACTGTTCTAGAATCCATACTTGATCCATTTGAAGGGTCTACCCCGTTT

GGC;

MuTA9bp_5IN (5' to 3'):
                                    (SEQ ID NO: 15)
TAACAATCAAGAAAAACAAGAAAATCGGACCTTCAAATGGGGTCTACCCC

GTTTGGC
and

MuTA9bp_3IN (5' to 3'):
                                    (SEQ ID NO: 16)
CAACTGTTCTAGAATCCATACTTGATCCATTTGAAGGGGTCTACCCCGTT

TGGC;

MuTA0bp_5IN (5' to 3'):
                                    (SEQ ID NO: 17)
TAACAATCAAGAAAAACAAGAAAATCGGACGGGTCTACCCCGTTTGGC
and MuTA0bp_3IN (5' to 3'):
                                    (SEQ ID NO: 18)
CAACTGTTCTAGAATCCATACTTGATCGGGTCTACCCCGTTTGGC,
``` respectively. The nMuta1 elements with different TSD lengths were then integrated into the 5'UTR of the ade2 gene on plasmid PWL89A.

Yeast Excision Assay

Plasmid PAG415GAL was transformed into yeast using the Frozen-EZ Yeast Transformation II Kit (Zymo research) and grown on CSM-leu with dextrose. The plasmid PWL89A was digested with restriction enzyme Hpa1, gel purified, then transformed together with purified DNA fragment of microelement or nonautonomous element into yeast cells containing PAG415GAL plasmid. Cells were grown in CSM-leu-ura with dextrose. Transformed yeast were grown to saturation (36-48 h) in 3 ml of CSM-his-leu-ura with dextrose, washed with 3 ml sterile water, resuspended in 0.5 ml water and plated onto CSM-ade-his-leu-ura with galactose as the sole carbon source. Colonies were counted after incubation at 30° C. for 15 days. Viable counts were made by plating 50 μl of a 1×10$^4$ dilution on yeast extract peptone dextrose plates. Excision frequencies of both the microelement and the nonautonomous element were determined by colony counts (FIG. 1D). Osm14 is a transposable element from the rice genome that served as a positive control. ADE2 revertant colonies were used to examine the footprints, primers ADE2CF 5'-CTGAC-AAATGACTCTTGTTGCA-GGGCTACGAAC-3' (SEQ ID NO:35) and ADE2CR 5'-TGGAAAAGGAG-CCATTAACGTGGTCATTGGAG-3' (SEQ ID NO:36) were used. If TSD were not included, various footprints were found after nMuta1 excision, when 8 or 9 bp TSDs were included, mostly perfect excision events were detected (FIG. 1A-C).

Yeast Integration Assay

To measure the integration frequency, yeast his3 gene was flanked by 350 bp from each end of Muta1 by overlapping PCR using primer Mu_His_5L, 5'-CGAAGCTGGAAAT-GTTTTAACTCTTGGCCTCCTCTAGTAC-3' (SEQ ID NO:19); Mu_His_5R, 5'-GTACTAGAGGAGGC-CAAGAGTTAAAACATTTCCAGCTTCG-3' (SEQ ID NO:20); Mu_His_3L, 5'-ATACGAACAGTATGA-TACTCAGGAAACTGATTATCTTGAG-3' (SEQ ID NO:21); Mu_His_3R, 5'CTCAAGATAATCAGTTTCCT-GAGTATCATACTGTTCGTAT-3' (SEQ ID NO:22). Different flanking TSDs were generated by PCR using primers MuTA8bp_5IN, MuTA8bp_3IN, MuTA9bp_5IN, MuTA9bp_3IN, MuTA0bp_5IN, MuTA0bp_3IN described earlier. This artificial element with different TSD sequence was cloned into the Hpa1 site in the exon of the ade2 gene on PWL89A vector. After growing to saturation in CSM-leu-ura medium, cells were washed with water and plated onto CSM-leu-ade and CSM-his-leu-ade plates with galactose (FIG. 1E). In another assay, single colonies from CSM-leu-ade with galactose plate were plated on CSM-his-leu-ade with dextrose plate, number of viable colonies were counted (FIG. 1F).

Genomic DNA of revertant colonies were extracted by the Yeastar genomic DNA kit (Zymo research), digested with Bfa1 and ligated with adaptors (5'-GACGATGAGTCCT-GAG-3' (SEQ ID NO:23) and 5'-TACTCAGGACTCAT-3' (SEQ ID NO:24)). PCR was performed with primers Bfa1+0 (5'-GACGATGAGTCCTGAGTAG-3' (SEQ ID NO:25)) and MuTD1 (5'-TTATGCCAAACGACTGTAT-3' (SEQ ID NO:26)). PCR products were used for a second round of PCR using primers Bfa1+0 and MuTD2 (5'-CCAAACGGGGTAGACCC-3' (SEQ ID NO:27)). Bands were gel purified and sequenced to obtain the insertion sites in the yeast chromosomes, then primers were designed flanking the insertion sites to recover the sequence at the site of insertion prior to insertion.

Excision frequencies of both the microelement and the nonautonomous element were determined by colony counts (FIG. 1A). Osm14 is a transposable element from the rice genome that served as a positive control. When TSDs were included in the reporter system, only perfect excision events were detected. If TSD were not included, various footprints were found after Muta1 excision (FIG. 1B). TE display and subsequent sequencing revealed that both elements were integrated into the yeast chromosomes and generated 8 bp or 9 bp TSDs upon insertion (Table 1). About 10% of the revertants analyzed had insertions at new loci and all eight characterized insertion sites are in exons of different yeast genes, accession number and TSDs are shown in Table 1 There appears to be no insertion sequence preference (data not shown).

TABLE 1

Insertion in yeast chromosomes.

| Donor TSD length | Insertion site | TSD sequence | Orientation | TSD length |
|---|---|---|---|---|
| 0 | intergenic | CCGGTTGA | + | 8 |
| 0 | intergenic | CTCTTGTT | − | 8 |
| 0 | intergenic | TTGATCAA | + | 8 |
| 0 | intergenic | GCATGGAA | − | 8 |
| 0 | intergenic | AGCTACAA | + | 8 |

TABLE 1-continued

Insertion in yeast chromosomes.

| Donor TSD length | Insertion site | TSD sequence | Orientation | TSD length |
|---|---|---|---|---|
| 0 | intergenic | AGACCAAT | − | 8 |
| 0 | intergenic | CTCTTTGC | − | 8 |
| 0 | intergenic | CAGGGCTGC | + | 9 |
| 0 | intergenic | TGCATGATA | + | 9 |
| 0 | intergenic | AAATTGATA | + | 9 |
| 0 | intergenic | CTCCCACAA | − | 9 |
| 0 | intergenic | TCCACCAAT | + | 9 |
| 0 | intergenic | GTGGGAATC | − | 9 |
| 0 | intergenic | GGATAGTTT | + | 9 |
| 0 | CDC15 gene | TGCGTCGT | − | 8 |
| 0 | RPS9D gene | GTCCACCA | + | 8 |
| 0 | PYC1 gene | ATTGGCTT | − | 8 |
| 0 | PRP1 gene | TATTGTCC | − | 8 |
| 0 | ERG13 gene | TTGGCTCT | + | 8 |
| 0 | CHZ1 gene | TTGATGGG | − | 8 |
| 0 | ATS1 gene | CCTATTATG | − | 9 |
| 0 | JEN1 gene | CTGTACTCC | + | 9 |
| 0 | YAP1801 gene | TTTCAATTG | − | 9 |
| 0 | AIM39 gene | CAGAATGAG | + | 9 |
| 0 | KIN2 gene | AGTGCGCTG | + | 9 |
| 0 | TAX4 gene | AGCAAGAGT | − | 9 |
| 0 | GTT1 gene | TTCTTACCA | − | 9 |
| 0 | MRPS35 gene | AACAGACGG | + | 9 |
| 0 | AQY2 gene | TAAGCATTG | − | 9 |
| 0 | unknown protein | GAATGTTCT | + | 9 |
| 0 | unknown protein | GAGAGTGAC | + | 9 |
| 8 | intergenic | CCTACCGA | − | 8 |
| 8 | intergenic | TTTCGTAG | − | 8 |
| 8 | intergenic | TTCGCGGAG | + | 9 |
| 8 | intergenic | GTACTCCTT | − | 9 |
| 8 | intergenic | GCTCTCATT | − | 9 |
| 8 | intergenic | GGCTAACAG | + | 9 |
| 8 | TAT1 gene | ATGCAGCA | − | 8 |
| 8 | unknown protein | CCATCTGG | − | 8 |
| 8 | THI3 gene | GGGGCTGAT | + | 9 |
| 8 | UPF3 gene | GAATAGTGA | − | 9 |
| 8 | OTU2 gene | GCATATCTC | − | 9 |
| 8 | SET5 gene | GCCATCTTC | − | 9 |
| 8 | SMF3 gene | CAGCTCCAA | + | 9 |
| 9 | intergenic | AATGGTTG | + | 8 |
| 9 | intergenic | CTAACTTCT | + | 9 |
| 9 | intergenic | CCATGTTAC | + | 9 |
| 9 | intergenic | ATATCGTCA | − | 9 |
| 9 | intergenic | CTAAAGGGC | − | 9 |
| 9 | intergenic | TTCTTCAGG | − | 9 |
| 9 | intergenic | GATGCATCG | − | 9 |
| 9 | HAP4 gene | AGTCTAGC | + | 8 |
| 9 | IRC20 gene | CATCCGAA | + | 8 |
| 9 | VRG4 gene | CTGTTTTC | − | 8 |
| 9 | STE12 gene | TTCCTGTA | + | 8 |
| 9 | KGD1 gene | CTAACCTC | + | 8 |
| 9 | SPT21 gene | CAAGGGCTC | + | 9 |
| 9 | WWM1 gene | CTGTGCTTG | − | 9 |
| 9 | CLB3 gene | CGGCTTAGA | + | 9 |
| 9 | HFM1 gene | AAAGTATTT | + | 9 |

Example 3. Interplasmid Transposition Assays in *D. melanogaster* and *A. aegypti* Developing Embryos Interplasmid transposition assays were used to show that Muta1 is highly active in both *D. melanogaster* and *A. aegypti* embryos. These assays included an internal control in which the transposition frequency of the piggyBac transposable element was simultaneously measured in these embryos, thereby permitting the activity of Muta1 to be measured against that of piggyBac. piggyBac was used as the control because it is routinely used to genetically transform species ranging from insects to mammals. High transposition activities of Muta1 relative to piggyBac indicate that Muta1 may have transpositional properties superior to piggyBac in these systems.

The Muta1 transposition assays employed three plasmids: a target plasmid, pDGV1 routinely used in assays of this type, an *Aedes Mutator* donor plasmid, and a Muta1 helper plasmid. The *Aedes Mutator* donor plasmid contained 348 bp of the left end and 346 bp of the right end of the element, each flanked by the 9 bp TSD present in the genome. The helper plasmid contained the cDNA from the Muta1 transposase placed under the control of the *D. melanogaster* hsp70 promoter. Both plasmids were injected into insect embryos at a concentration of 250 µg/ml. The target plasmid was injected at a concentration of 500 µg/ml.

The data presented in Table 2 demonstrated that Muta1 is active in the embryos of both species. In *D. melanogaster*, its activity is essentially equivalent to that of piggyBac. In *A. aegypti*, it exceeds the activity of piggyBac by approximately 20-fold.

TABLE 2

Mutal activity in D. melanogaster and A. aegypti.

| Insect Species | No. of Expts. | No. of Embryos Injected | Muta1 Donor Plasmid | PiggyBac Donor Plasmid | Muta1 Transpositions | PiggyBac Transpositions | Muta1 Frequency | Piggybac Frequency |
|---|---|---|---|---|---|---|---|---|
| D. melanogaster | 4 | 444 | 127,200 | 154,400 | 51 | 69 | $4.01 \times 10^{-4}$ | $4.47 \times 10^{-4}$ |
| A. aegypti | 2 | 120 | 136,000 | 160,800 | 1,234 | 74 | $9.10 \times 10^{-3}$ | $4.60 \times 10^{-4}$ |

The junction fragments of 21 Muta1 integrations recovered from the D. melanogaster injections were determined. The target insertion site and site duplication sequences and lengths are shown in Table 3. All but three generated 9 bp TSDs. Only two inserted into the same site in the target plasmid (jw16 and jw19) and so may not be independent events. Of the three with 8 bp TSDs, the final mismatched nucleotide is shown as a capital letter in Table 3.

TABLE 3

D. melanogaster target site sequences and lengths.

| Sample | Orientation in Target Plasmid | Insertion Site (bp) | Target Site Duplication Sequence | Target Site Duplication Length |
|---|---|---|---|---|
| jw1 | negative | 316 | cataaaatc | 9 |
| jw2 | negative | 2000 | ctctagagT | 8 |
| jw3 | negative | 827 | gtttcaaaa | 9 |
| jw4 | negative | 1022 | gtttttgca | 9 |
| jw5 | negative | 2009 | ccggggatc | 9 |
| jw6 | positive | 2199 | gttggaatg | 9 |
| jw7 | negative | 2172 | tgttctata | 9 |
| jw8 | positive | 592 | tgataaagc | 9 |
| jw9 | negative | 2040 | gtggcaaag | 9 |
| jw10 | positive | 725 | gttgaagtt | 9 |
| jw11 | positive | 886 | tgaagaagg | 9 |
| jw12 | negative | 2232 | ctaacaagT | 8 |
| jw13 | negative | 895 | gccttcttc | 9 |
| jw14 | negative | 228 | gtaaaaaaa | 9 |
| jw15 | negative | 2402 | gtacatact | 9 |
| jw16 | positive | 2184 | cgagaaaac | 9 |
| jw17 | positive | 409 | agtaaaagC | 8 |
| jw18 | negative | 2555 | gtcgttcac | 9 |
| jw19 | positive | 2184 | cgagaaaac | 9 |
| jw20 | positive | 398 | gaatatgac | 9 |
| jw21 | negative | 675 | ctaataaat | 9 |

These data confirmed that Muta1 transposes in D. melanogaster and that, upon transposition, the transposed sequence is delimited by the ends of the transposon and the 9 bp TSDs. The consensus TSD shows a weak preference for A nucleotide at the 6th and 7th positions.

The junction fragments of 18 Muta1 integrations recovered from the A. aegypti injections were determined. Table 4 shows the insertion site and TSD sequences and lengths. All generated a 9 bp TSD and all were independent.

TABLE 4

A. aegypti target site sequences and lengths

| Sample | Orientation in Target Plasmid | Insertion Site (bp) | Target Site Duplication Sequence | Target Site Duplication Length |
|---|---|---|---|---|
| 1, 19 | positive | 580 | CTACGCAAT | 9 |
| 2, 20 | negative | 2296 | CCTACAGGG | 9 |
| 3, 21 | positive | 15 | AATCTTGTA | 9 |
| 4, 22 | positive | 198 | CTAATAGCC | 9 |
| 5, 23 | positive | 979 | AATGAAATC | 9 |
| 6, 24 | negative | 886 | CCTTCTTCA | 9 |
| 7, 25 | positive | 2551 | GTTTGTGAA | 9 |
| 8, 26 | negative | 349 | GTTTGTAAT | 9 |
| 9, 27 | positive | 676 | ATTTATTAG | 9 |
| 10, 28 | positive | 306 | CTGATTTTA | 9 |
| 11, 29 | negative | 554 | TTCAAAATC | 9 |
| 12, 30 | positive | 411 | TAAAAGCAG | 9 |
| 13, 31 | positive | 322 | TACTGGAAT | 9 |
| 14, 32 | positive | 907 | ACTTGAAAG | 9 |
| 15, 33 | positive | 336 | GGCTTTGGG | 9 |
| 16, 34 | positive | 920 | GCTAAATAT | 9 |
| 17, 35 | positive | 699 | AACAAGAAC | 9 |
| 18, 36 | positive | 515 | ATGGAAGAT | 9 |

As observed in D. melanogaster, these data confirmed that Muta1 transposes and that, upon transposition, the sequence transposed is delimited by the ends of the transposon and the 9 bp TSD. The consensus TSD shows no strong sequence preference.

In summary, the illustrative data presented in Examples 2 and 3 demonstrated the activity of Muta1 in yeast and two insect species. Notably, it has a high transposition frequency, much higher than piggyBac in A. aegypti. While only a sampling of potential transpositions recovered from each species were evaluated, the fact that the overwhelming majority were confirmed by DNA sequencing of their junction fragments validated the high activity of Muta1.

Example 4. Muta1 can Excise and Integrate in Human Cells

The piggyBac transposon from the cabbage looper, *Tricoplusia ni*, has been developed as a vector for use in human gene therapy and we therefore wished to determine if Muta1 was also active in human cells. In this example, a genetically tagged Muta1 element was placed into the genome of both HeLa and HEK392 cells. It was then determined whether Muta1 could excise and, if so, whether precise excisions could be recovered, as was seen in *D. melanogaster* and *A. aegypti* using plasmid-based excision assays. Precise excisions were recovered from both human cell types, 4/26 excisions recovered from HeLa cells were precise while 6/28 excisions recovered from HEK392 cells were precise (FIG. 2). Thus, while Muta1 shares with piggyBac the ability to precisely excise from the human genome, unlike piggyBac precise excisions are a minority of excision events recovered. Precise excisions of Muta1 were recovered with approximately the same frequency as excision events in which one intact copy of one TSD and one lacking the terminal 4 bp were observed (FIG. 2).

Muta1 activity was examined in HeLa cells using both interplasmid transposition assays and by detecting integration into the human genome. Muta1 integrated into the target plasmid generated 9 bp TSDs in 21/24 of the transpositions characterized, with the remaining three generating 8 bp TSDs (Table 5). There was a very weak preference for A at positions 4, 6 and 7 within the 9 bp TSD.

TABLE 5

Target Site Duplications (TSDs) and locations of Muta1 transpositions into target plasmid in HeLa cell culture.

| Insertion Site in Target Plasmid (bp) | TSD Sequence | Orientation | TSD Length (bp) |
|---|---|---|---|
| 43 | TATTTAAAT | − | 9 |
| 71 | GGGTGAGCG | + | 9 |
| 195 | ACTCTAATA | + | 9 |
| 216 | AAAAATTAC | − | 9 |
| 219 | TAAAAAAAT | − | 9 |
| 242 | ACTTAATTC | − | 9 |
| 566 | GATTTGAGT | + | 9 |
| 649 | CCAAAATAT | − | 9 |
| 744 | GCCATAAAT | − | 9 |
| 769 | GAAAAGAGA | + | 9 |
| 809 | GTGTAAATC | − | 9 |
| 1991 | TCTAGAGTC | − | 9 |
| 2044 | CGCAAAAAA | − | 9 |
| 2099 | TCTGAATAT | − | 9 |
| 2239 | GGTTGGACT | + | 9 |
| 2264 | CCAAGAAAG | + | 9 |
| 2287 | CTTTATGTG | − | 9 |

TABLE 5 -continued

Target Site Duplications (TSDs) and locations of Muta1 transpositions into target plasmid in HeLa cell culture.

| Insertion Site in Target Plasmid (bp) | TSD Sequence | Orientation | TSD Length (bp) |
|---|---|---|---|
| 2317 | CAATTTCCT | − | 9 |
| 2388 | CAAGTAAG | + | 8 |
| 2402 | AACACCAAG | − | 9 |
| 2471 | GGTCTAATC | − | 9 |
| 2482 | CAAAAGAC | − | 8 |
| 2482 | TCAAAAGAC | − | 9 |
| 2495 | GTTATATT | + | 8 |

Figure 3:
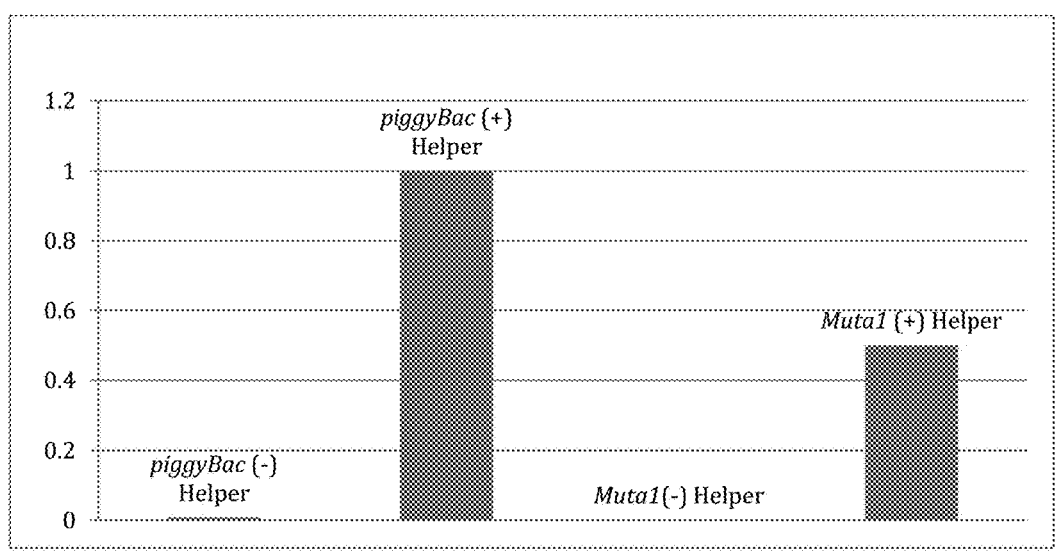
FIG. 3 provides illustrate data for Muta1 transposition activity into HeLa chromosomes.

Integration into human chromosomes was next assayed by placing a drug resistance gene between the same Muta1 ends used for the interplasmid transposition assays and determining integration frequency by selecting for cells that grew in media supplemented with antibiotic. The same experiments were simultaneously performed with piggyBac and it was determined that Muta1 integrated into the human genome at a frequency approximately half that of the piggyBac element (Table 6, FIG. 3). Negligible levels of transposition of either Muta1 or piggyBac were detected in the absence of their respective transposases. Analysis of 20 Muta1 integrations confirmed transposition into human genomic DNA (Table 7). Comparison of insertion data into the pGDV1 target plasmid obtained from insect and human transposition assays showed that Muta1 inserted into many sites within the plasmid consistent with it not having a strong or moderate bias for sequence preference (data not shown). This supports the use of Muta1 as a gene and enhancer trapping tool in animals.

TABLE 6

Muta1 Transpositions into the HeLa Genome

| Transposase | Transposon | No. of expts. | No of Colonies* (std. dev.) |
|---|---|---|---|
| Muta 1 | Muta1 | 3 | $4.9 \times 10^{-1}$ ($4.1 \times 10^{-2}$) |
| — | Muta1 | 3 | $7.0 \times 10^{-3}$ ($4.5 \times 10^{-3}$) |
| piggyBac | piggyBac | 3 | 1.000 |
| — | piggyBac | 3 | $7.7 \times 10^{-3}$ ($1.3 \times 10^{-3}$) |

*Normalized to the number of colonies arising from piggyBac transpositions)

TABLE 7

Muta1 integrations into the HeLa genome 9-17-13

| Integration # | Chromosome | Sequence ID | Gene | Location | Strand/ORF |
|---|---|---|---|---|---|
| RH41 | 1 | ref|NW_004077999.1| | | Inserted 99 bp 5' to tRNAVal gene | Plus/Minus |
| RH3 (8-28-13) | 1 (and others) | ref|NW_001838533.2| | Repeated sequence | Intergenic | Plus/Plus |
| RH38 | 2 | ref|NW_004078005.1| | | Intergenic | Plus/Plus |
| RH33 | 2 | ref|NG_027786.1| | Cell cycle 27 homolog pseudogene | mRNA | Plus/Plus |
| RH36 | 4 | gb|AC097381.3| | Actin binding LIM protein family, member 2 | Intron | Plus/Minus |
| RH13 (8-28-13) | 5 | ref|NT_023133.13| | RMND5B required for meiotic nuclear division 5 homolog B (*S. cerevisiae*) | Intron | Plus/Plus |
| RH42 | 6 | ref|NW_004078026.1| | | Intergenic | Plus/Minus |
| RH11(8-28-13) | 6 | ref|NT_007592.15| | | Intergenic | Plus/Plus |
| RH23 | 8 | gb|AF189005.5| | FAM10B - unannoted | mRNA | Plus/Plus |
| RH24 | 8 | ref|NW_004929337.1| | VPS37A (vascular protein sorting 73 homolog 1 (*S. cerevisiae*) | Intron | Plus/Plus |
| RH1 (9-4-13) | 9 | ref|NT_008413.18 | lysine-specific demethylase 4C isoform 4 | intron | Plus/Plus |
| RH31 | 10 | ref|NG_029917.1| | Ankyrin 3 | Intron | Plus/Minus |
| RH5 (9-4-13) | 10 | ref|NW_004929370.1 | uncharacterized LOC399715 | Intron | Plus/Plus |
| RH43 | 19 | ref|NW_001838498.2| | Leukocyte receptor cluster member 8 | 3'UTR | Plus/Minus |
| RH25 | 19 | ref|NW_004929415.1| | | Intergenic | Plus/Plus |
| RH6(8-28-13) | 22 and 21 | ref|NG_027786.1| | Cell cycle 27 homolog pseudogene | mRNA | Plus/Minus |
| RH3 | X | emb|Z86064.2| | | Intergenic | Plus/Plus |
| RH2 (8-28-13) | Unknown-Multiple locations | gb|AC234849.2| | Repeated sequence | | |
| RH5 (8-28-13) | Unknown-Multiple locations - at least 21 and 22 | ref|NT_167214.1| | Repeated sequence | | |
| RH3 (9-4-13) | Unknown | ref|XM_005274803.1| | *Homo sapiens* serine/arginine repetitive matrix protein 2-like | mRNA | Plus/Plus |

Materials and Methods for Example 3

Excision of Muta1 in HeLa and HEK392 Cells.

Muta1 Excision Assay Element: A Muta1 transposition event (from plasmid pMuta1 donor) with 9 bp TSDs in the target plasmid pGDV1 (obtained in the HeLa cell transposition experiments) was amplified by PCR to contain target site duplications flanked by AgeI sites. PCR primers were as follows: Muta1 33 Forward: 5'-GATACCGGTCTTGT-TAGCGAGTTGGTTGGACT-3' (SEQ ID NO:28) and Muta1 33 Reverse: 5'-AATACCGGTGGATTAATC-CCAATTCAAGTCCAAC-3' (SEQ ID NO:29). Amplification with Phusion DNA polymerase (New England Biolabs) was performed using the following settings: 98° 30 sec, 5× (98° 08", 60° 15", 72° 1.5'), 30×(98° 08", 72° 1.5'), 72° 7', 4°. The PCR product was cloned into pJet1.2 (Fermentas) and the sequence verified. The pJet event 33 clone was digested with AgeI (Fermentas) and the fragment containing the Muta1 ends with the 9 base target site duplications was used as the donor element below.

Construction of Excision Assay Donor:

The plasmid pBacDNeo (reference) was digested with restriction enzymes HincII and XhoI (Fermentas). pCMV-EGFP (reference) was digested with SalI and PvuII and the fragment containing the CMV promoter and the EGFP gene was purified on an agarose gel and ligated to the pBacDNeo vector fragment to create plasmid pBacDNeoEGFP. The AgeI site between the CMV promoter and the EGFP ORF was digested and ligated to the Muta1 element described above flanked by AgeI sites (see above) to create the plasmid pBDNeoM1X.

Cell Lines and Transformation:

HeLa and HEK392 human cell lines were grown as above in DMEM supplemented with 10% FBS. Cells were seeded at 500,000 cells per well of 6-well plates and allowed to grow overnight. Cells were transfected with plasmid pBDNeoM1X using XtremeGeneHP (Roche) and allowed to recover for two days at 37° C. Cells were then treated with trypsin, diluted 1:3 and 1:30, and 2.5 ml of cells were added/well in 6-well plates in the presence of 750 ug/ml Geneticin (Invitrogen). Media was changed after 1 week, and selection was continued for an additional week. After selection the cells were maintained in media containing 500 ug/ml Geneticin. These transformed cells were seeded into 24-well plates at 80,000 cells/well in 250 ug/ml geneticin and allowed to grow overnight. After replacement of media with fresh complete medium (minus geneticin), cells were transfected with pCMV-Muta1 helper plasmid or control plasmid pUC19. Cells were allowed to grow for two days before harvesting cells for DNA. DNA was purified independently from each well using the DNeasy Blood and Tissue Kit (Qiagen).

Amplification of Muta1 Excision Events:

Excision products were amplified using a nested PCR strategy. Amplification was first carried out with Q5 Hot Start DNA Polymerase (New England Biolabs) using the primers pBac Excision For. 2: 5'-CGCATGTGTTTTATCG-GTCTGTATATCGAGG-3' (SEQ ID NO:30) and SV40 Excision Rev. 1A: 5'-CCCATCACAAAGCTCTGACCT-CAATCC-3' (SEQ ID NO:31). PCR conditions were as follows: 98° 30 sec, 35× (98° 08", 66° 15", 72° 75 sec), 72° 2', 4°. PCR products were diluted 1:500 and then amplified using Taq DNA Polymerase (Bioland) with the primers Excision 1 For.: 5'-GCTAACTAGAGAACCCACTGCT-TACTG-3' (SEQ ID NO:32) and Excision 1 Rev.: 5'-TGCA-GATGAACTTCAGGGTCA-3' (SEQ ID NO:33) and the PCR conditions: 94° 3', 20× or 30× (94° 20", 60° 15", 72° 15 sec), 72° 5', 4°. PCR products were cloned into pJet1.2 and sequenced. Generally 3 clones were sequenced from each template from an experimental well. Only unique sequences from a given template were used in the analysis-identical sequences were discarded.

Transposition Assays in HeLa Cells:

HeLa cells were transfected using FuGene6 with 0.125 ug each of pPWA-CMV-PB (PNAS), pBac-GO-EGFP, pCMV-Muta1, pBSMuta1-GenOriLacZ, and 0.5 ug of pGDV1. In some assays 0.25 ug each of the Muta1 donor and helper were transfected along with the target. Two days post-transfection plasmids were isolated as from our embryo assays and transformed into E. coli and plated as above. Chromosomal integration assays in HeLa cells were performed as previously described (Li, et al., Proc. Natl. Acad. Sci. USA 110:E478-87, 2013; Epublished Oct. 22, 2012).

Example 4. Muta1 can Genetically Transform Drosophila melanogaster

The Muta1 transposon can be used to genetically transform D. melanogaster. One of two different genetic markers (white or dsRED) was placed inside a Muta1 transposon containing 348 bp of the left end of the transposon (containing the 146 bp direct repeats of the TIR) and 346 by of the right end of the transposon (containing the 146 bp of the TIR). A plasmid containing this transposon was co-injected with a second plasmid containing the Muta1 transposase gene placed under the control of the D. melanogaster hsp70 heat shock gene into pre-balstoderm D. melanogaster embryos following standard protocols. Surviving adult progeny were backcrossed and their progeny screened for the presence of the appropriate genetic marker (white or dsRED) in their eyes. Progeny expressing the marker were self-crossed to generate transgenic lines.

Genomic DNA prepared from transgenic lines was analyzed for evidence of transpositional recombination by the Muta1 transposon, specifically the presence of the Muta1 transposon flanked by 8 or 9 bp TSDs in the genome. Transgenic D. melanogaster were achieved using either marker at frequencies of 5.6% (white) and 11% (dsRED) (Table 8). Analysis of the junction fragments of the Muta1 transposon in these transgenic lines confirmed that all of the Muta1 transposon had integrated and that the sequences integrated were delimited by the TIRs of the element generating the predicted 9 bp TSDs. These data are entirely consistent with integration of the Muta1 transposon by transpositional recombination.

TABLE 8

Genetic transformation of D. melanogaster using the Muta1 transposon.

| Muta1 Transposon | No. of Embryos Recovered | No. of Surviving Adults | No. of Fertile Crosses | No. of Transgenic Progeny | Transformation Frequency |
| --- | --- | --- | --- | --- | --- |
| Muta1 [white] | 40 | 21 | 18 | 1 | 5.6% |
| Muta1 [dsRED] | 60 | 45 | 27 | 3 | 11.1% |

Example 5. Muta1 is Mobile within the Genome of D. Melanogaster

The Muta1 transposon can be remobilized in D. melanogaster. We constructed two transgenic lines of D. melanogaster; one containing a piggyBac transposon into which the Muta1 transposase gene placed under the control of the D. melanogaster had been inserted. The second transgenic line contained the Muta1 transposon into which the Muta1 transposase gene under the control of the D. melanogaster hsp70 promoter has been inserted. Each transposon contained a different genetic marker, EFGP or dsREd, under the control of the optic nerve-specific 3×P3 promoter. Crossing homozygotes from each line allow the mobility of each transposon to be tracked based on changes in expression of the relevant genetic marker. Our preliminary data show that Muta1 is remobilized in D. melanogaster and so could be used as a genetic tag or trap in this species.

Example 6. Muta1 can Genetically Transform Aedes Aegypti

Five transgenic lines of A. aegypti using the Muta1 transposon have been generated, four using the wild-type form of the Muta1 transposase and one using a synthetic "stealth" form of the Muta1 transposase that was engineered to evade small RNAs that may target the element. This was designed based on an analysis of A. aegypti piRNAs identical to Muta1 that were present in ovarian and germline tissue of A. aegypti. The ORF of the stealth form of Muta1 was designed so that there was likely to be insufficient homology between the piRNAs and the coding region of Muta1 to allow for the piRNAs to recognize the Muta1 transcript and so inactivate it. Both the stealth transposase form and native form of the transposase are functional. Muta1 is the fourth transposon known to transform *A. aegypti* and is the first *A. aegypti* transposon to be shown to be functional in its host.

Example 7. Activity of Muta1 in *Saccharomyces cerevisiae*

Activity of Muta1 was assessed in yeast, *Saccharomyces cerevisiae*. Results are shown in Table 9. The data presented in Table 9 demonstrated that the Muta1 transposase catalyzed precise excision of the Muta1 transposon thus further confirming the observations from *Drosophila melanogaster* and *Aedes aegypti*.

TABLE 9

Muta 1 Precise excision in yeast

| TSD sequence | No. Excision events | No. Precise excision |
|---|---|---|
| TTCAATAG | 20 | 18 |
| CGATTCAA | 19 | 18 |
| GGTAACTC | 21 | 21 |
| ATTCAATAG | 20 | 19 |
| TCGATTCAA | 20 | 20 |
| CGGTAACTC | 19 | 17 |

The illustrative data provided in these examples thus demonstrate the ability of Muta1 to excise precisely in various eukaryotic genomes.

Example 8. Expression and Activity of Purified Muta1 Protein

The Muta1 transposase was expressed in *E. coli* and purified. Activity of the purified Muta1 protein was determined using a strand cleavage assay in which the Muta1 protein and end-labeled DNA that included the transposon end and flanking DNA were incubated together and strand cleavage determined. The assay results (data not shown) showed cleavage between the transposon end and the flanking DNA, thus indicating that the purified Muta1 protein retained its biochemical activity.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant expression vector comprising a polynucleotide encoding a Muta1 transposase having at least 95% amino acid sequence identity to SEQ ID NO:2.

2. The expression vector of claim 1, wherein the Muta1 transposase comprises the amino acid sequence of SEQ ID NO:2.

3. An isolated recombinant host cell comprising the expression vector of claim 1.

4. A recombinant vector comprising a heterologous nucleic acid comprising a Muta1 transposon, wherein the Muta1 transposon comprises a 5' inverted terminal repeat comprising the nucleotide sequence of SEQ ID NO:3 and a 3' inverted terminal repeat comprising the nucleotide sequence of SEQ ID NO:4, wherein the 5' and 3' inverted terminal repeats flank a nucleic acid sequence to be inserted into a target polynucleotide.

5. The recombinant vector of claim 4, wherein the nucleic acid sequence to be inserted into a target polynucleotide is a marker gene.

6. The recombinant vector of claim 5, wherein the marker gene encodes a fluorescent protein.

7. A gene transfer system comprising:
a recombinant expression vector comprising a polynucleotide encoding a Muta1 transposase having at least 95% amino acid sequence identity to SEQ ID NO:2; and
a nucleic acid comprising a Muta1 transposon, wherein the Muta1 transposon comprises a 5' inverted terminal repeat comprising the nucleotide sequence of SEQ ID NO:3 and a 3' inverted terminal repeat comprising the nucleotide sequence of SEQ ID NO:4, wherein the 5' and 3' inverted terminal repeats flank a nucleic acid sequence to be inserted into a target polynucleotide; and further, wherein the nucleic acid comprising the Muta1 transposon is contained in the recombinant expression vector comprising the polynucleotide encoding the Muta1 transposase or is contained in a separate recombinant vector.

8. The gene transfer system of claim 7, wherein the Muta1 transposase comprises the amino acid sequence of SEQ ID NO:2.

9. The gene transfer system of claim 7, wherein the polynucleotide encoding the Muta1 transposase and the nucleic acid comprising the Muta1 transposon are contained in separate recombinant vectors.

10. A method of introducing a nucleic acid sequence of interest into a target polynucleotide, the method comprising introducing a Muta1 transposon nucleic acid into a host cell that comprises a heterologous Muta1 transposase comprising the amino acid sequence of SEQ ID NO:2; wherein the Muta1 transposon nucleic acid comprises a 5' inverted terminal repeat comprising the nucleotide sequence of SEQ ID NO:3, a 3' inverted terminal repeat comprising the nucleotide sequence of SEQ ID NO:4, and a nucleic acid sequence of interest to be inserted into the target polynucleotide, said nucleic acid sequence of interest flanked by the 5' and 3' inverted terminal repeat sequences.

11. The method of claim 10, wherein the host cell is a vertebrate host cell.

12. The method of claim 11, wherein the vertebrate host cell is a mammalian cell.

\* \* \* \* \*